(12) United States Patent
Taparia et al.

(10) Patent No.: US 11,963,904 B2
(45) Date of Patent: Apr. 23, 2024

(54) INSTRUMENT TO PREPARE AND SAFELY PLACE AN INTRA-UTERINE DEVICE

(71) Applicant: Pregna International Limited, Mumbai (IN)

(72) Inventors: Mukul Taparia, Mumbai (IN); Ajit Raje, Mumbai (IN); Prateek Jain, Pune (IN); Dhawal Goyal, Pune (IN)

( * ) Notice: Subject to any disclaimer, the term of this patent is extended or adjusted under 35 U.S.C. 154(b) by 362 days.

(21) Appl. No.: 17/401,837

(22) Filed: Aug. 13, 2021

(65) Prior Publication Data

US 2022/0087856 A1    Mar. 24, 2022

(30) Foreign Application Priority Data

Sep. 23, 2020 (IN) .............................. 202021041234

(51) Int. Cl.
*A61F 6/18* (2006.01)
*A61F 6/14* (2006.01)

(52) U.S. Cl.
CPC ................ *A61F 6/18* (2013.01); *A61F 6/144* (2013.01)

(58) Field of Classification Search
CPC .... A61F 6/14; A61F 5/453; A61F 6/18; A61F 6/146; A61F 6/04; A61F 2006/048; A61F 6/12; A61B 5/4368; A61B 46/30; A61B 46/00; A61B 17/42; A61B 2017/1205; A61K 9/0036; A61K 9/0039
See application file for complete search history.

(56) References Cited

U.S. PATENT DOCUMENTS 9,949,870 B2 * 4/2018 Frankenne ................ A61F 6/18

* cited by examiner

*Primary Examiner* — Ophelia A Hawthorne
(74) *Attorney, Agent, or Firm* — Ifica D. Mehra

(57) ABSTRACT

An instrument to prepare and safely place an intra-uterine device in uterus of a woman, comprising a dynamic stopper, a string management arrangement whereby a string of an IUD is in one of a locked condition or an unlocked condition, an operating device, further comprising a base, a cover a carriage, wherein the dynamic stopper slidably resides in the base and can slide by the sliding length, wherein the string exits from an outpoint and re-enters from an inpoint, the outpoint is at a trim length and the inpoint is at a conservative length. The string can be trimmed as per sounding measurement of uterus of woman, before inserting the instrument in uterus and string entanglement possibilities are eliminated, irrespective of type of IUD.

15 Claims, 33 Drawing Sheets

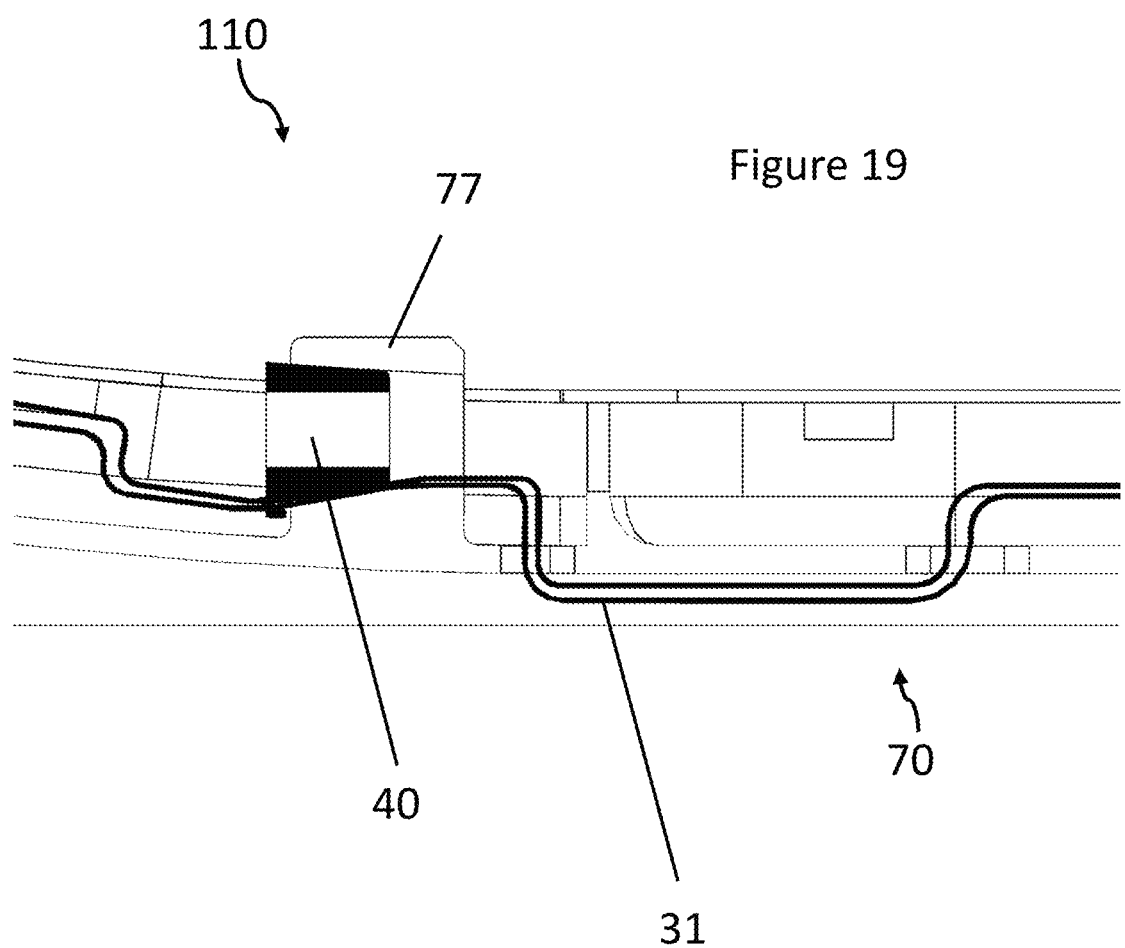

INSTRUMENT TO PREPARE AND SAFELY PLACE AN INTRA-UTERINE DEVICE

CLAIM OF PRIORITY

This application claims priority to Indian Provisional Patent Application No. 202021041234 filed on 23 Sep. 2020, titled "AN INSTRUMENT TO PREPARE AND SAFELY PLACE AN INTRA-UTERINE DEVICE".

FIELD OF THE INVENTION

The present invention relates to an intra-uterine device, particularly to an instrument which is to load and insert the intra-uterine device and the process of loading, inserting and safely placing the intra-uterine device in the uterus of a woman, hygienically.

BACKGROUND OF THE INVENTION

There are several female contraceptives available. An intra-uterine device (herein after abbreviated as IUD) is a long-term or medium-term contraceptive which is placed in the uterus of female. Most commonly available IUDs are in the shape of the English letter "T" since this shape is found appropriate to the shape of uterus.

While the IUDs are required to be in the shape of "T", they cannot be inserted in this form as the opening of the cervix is small. For this reason, all IUDs use an insertion instrument for insertion and proper location of the IUD. Arms forming "T" of IUD are folded either upwards or downwards so that IUD can be contained in the opening of a narrow tube/inserter which then can be inserted in the uterus. This process of folding the IUD so that the instrument/inserter is ready to insert is known as loading or preparing the IUD.

Loading or preparing of IUD needs to be done minutes before it is required to be inserted in uterus, and if done earlier, or if supplied duly loaded, then the IUD shall not return to the desired "T" shape in uterus and shall not work effectively. Due to this requirement, the process of loading has to be performed by service providers just prior to inserting and placing IUD in uterus.

Up-folding IUDs and down-folding IUD have a significant difference in their preparation and placement procedure. Upfolding IUDs implies that arms forming "T" are together while stem of IUD is below folded arms. This may be easily understood from FIGS. 1A to 3B of U.S. Pat. No. 5,785,053A. Patent application US2013/0014762(A1) also comprehensively covers an upfolding IUD. Down-folding implies that arms forming "T" as well as stem of IUD are together. This may be easily understood from FIGS. 7 and 9 of U.S. Pat. No. 4,143,656.

There is a significant difference in process of inserting and placing an up-folding IUD and a down-folding IUD in uterus. While placing an upfolding IUD, the arms of the "T" start unfolding downwards as soon as IUD is made to gradually eject out of the instrument. Person placing such upfolding IUD takes a pause to allow the upfolding arms to unfold at their own pace before finally placing IUD in uterus, lest ends of arms of IUD gets entangled with side walls of uterus, preventing a far end of IUD to reach fundus! On the other hand, when placing a downfolding IUD, there is no such precaution needed as the arms of IUD unfold upwards at their own natural pace while a far end of the IUD touches fundus.

In other words, an upfolding IUD is easier to load and difficult to place in uterus, while a downfolding IUD is relatively more difficult to load and relatively easier to place.

Patent application number U.S. Ser. No. 15/745,579 discloses an instrument to load a downfold IUD without human maneuvering. US 2018/0055684 A1, on the other hand discloses another instrument suitable for upfolding IUDs.

Prior art like U.S. Ser. No. 10/028,858, US2019/0307600 continue to ignore that a string attached to the IUD substantially stays in the instrument when the IUD is just placed in the uterus and the instrument is being withdrawn. Therefore, string entangling in the instrument remains a potential cause of disturbing safe placement of IUD in the uterus. Importantly, it is left to the service provider to randomly stop intermittently while inserting an upfolded IUD!

Such instruments being for one-time use, cost is an important factor.

Present invention effectively and economically addresses loading or preparation of upfolding IUDs for subsequent insertion and safe placement in uterus.

Objectives

The objective is to invent an instrument to load or prepare an intra-uterine device hygienically.

Another objective is to invent a simple instrument to load or prepare an intra-uterine device which is upfoldable.

Yet another objective is to invent an instrument which is capable of loading the intra uterine device in a consistent manner.

Yet another objective is to invent an instrument that causes minimal trauma to woman.

Yet another objective is to invent an instrument that ensures a horizontal orientation of the IUD, while the instrument may operate from an either horizontal orientation.

Yet another objective is to ensure suture release mechanism that ensures that the suture/thread/string is never stuck anywhere after deployment.

Yet another objective is to ensure single hand operation for insertion, deployment and retraction steps of the instrument.

Yet another objective is to ensure prevent accident or injury during insertion in any case to avoid perforation of fundus.

Yet another objective is to invent an instrument which is economical and effective.

Yet another objective is to achieve multiple stages of complete process with a single hand and knob movement.

Yet another objective is to eliminate and or minimize the guesswork of the user operation while preparing/loading, deployment/release.

Yet another objective is to prepare string length prior to insertion, according to uterus size of woman.

SUMMARY OF INVENTION

The instrument according to present invention comprises a "T" shaped intra-uterine device, a graduated tube, a push rod inside the graduated tube, a dynamic stopper with a flange, operated by an operating device. The instrument further comprises a string management arrangement. The string of the IUD is in an unreleased or a locked condition, and taut between the lower end and the operating arrangement, when the instrument is received by a medical service provider. In the present invention, the string is NOT required to be pulled/manipulated by the medical service provider for loading or preparing the instrument. The process of loading, inserting in uterus and safely releasing the IUD is carried out by a single hand operation.

The dynamic stopper is a tubular channel having the flange. There are provided guide paths at least on two alternate faces of the dynamic stopper. A sliding length of the dynamic stopper is commensurate with an arm length of the arms of the IUD. A diameter of the tubular channel allows a passage of the graduated tube tightly.

The operating device comprises a base, a cover, an operating knob, a carriage. The base has an open neck construction with a collar and a first flange guiding projections. There are carrier guiding projections. On an inside of walls is provided an array of continuous incline and notches alternately for a prescribed length. There are a plurality of cover engagement means on both the walls. A tube guideway, also provided is a string socket with a hole. The base is slightly curvatured.

The carriage has at least a pair of locking tooth on an either side. The travel slot has an assembly opening which is wider than the travel slot. There is provided a string plug on a lower side. At the operator end of the instrument is a pushrod passageway with a seat.

The operating knob has a thumb surface and at least a pointer on an either knob side. There is provided a hanging tubular construction on an opposite side of the thumb surface. The tubular construction has a larger diameter part having a pair of pusher, and a smaller diameter part.

The cover has a slot, an open complementing neck construction, a second flange guiding projections, and a plurality of base engagement means equal in number of the cover engagement means. A knob markings are provided on an external side of the cover. The cover is slightly curvature in accordance with the base.

The pushrod is a slender cylinder, has a collar, a reversibly collapsible fitment means at its operator end and a flat surface at the IUD end.

The graduated tube is a thin walled hollow cylinder having an edge at the IUD end, a measurement markings and a string exit slot.

In the instrument that is ready to use, the dynamic stopper slidably resides in the base free to slide along the guide paths constrained by the first flange guiding projections and or the second flange guiding projections, and can slide by the sliding length. The operator end of the graduated tube is slided with a little force through the tubular channel of the dynamic stopper, till the operator end of the graduated tube is disposed firmly in the larger diameter part of the knob. The dynamic stopper rides on the graduated tube. The hanging tubular construction of knob resides in the travel slot of the carriage. The push rod largely resides inside the graduated tube with the reversible collapsible fitment means of the pushrod pushed in the pushrod passageway such that the collar of the pushrod sits in the seat of the carriage. The stem of the IUD sits in the graduated tube at its IUD end, while the string is slipped in and exits from the string exit slot and is trapped between the string plug and the string socket while keeping it tautly pulled out from the hole, thus the string is in the unreleased or the locked condition. The terminating ends of the string are contained inside of the base near its operator end.

For use of the instrument, when the knob is made to slide towards the IUD end, the graduated tube and the dynamic stopper also travel towards the IUD end. The dynamic stopper travels forward by the sliding length while the graduated tube engulfs the arms of the IUD till the edge of the graduated tube is stopped by the dome shaped ends of the arms having come almost together. Further sliding of the knob towards the IUD end causes the carriage to also move towards the IUD due to the pusher of the knob, and consequently the pushrod also correspondingly moves. A movement of the carriage towards the IUD end causes the string plug to move away and thus unplug from the string socket and the string is in an unlocked or a released condition.

Importantly, due to the inventive dynamic stopper that moves equivalent to arm length, the medical service provider doesn't have to approximate intermediate stop and partial release of the IUD as is prevalent in prior art products.

In another embodiment, the string management comprises a floating cone floatingly disposed on the graduated tube and a tubeway integratedly provided on the base.

The floating cone has a tubular hole on an inside and a conical frustum on an outside. There is provided a hook on the IUD side of the floating cone. The tube way has an inner cylindrical path through which the graduated tube passes clearly, while the floating cone gets seated firmly in the tube way like any known plug and a socket arrangement.

In the instrument as per second embodiment that is ready to use, the string is wrapped around the hook by several turns, slid through the tubular hole and the tubeway taut, while the floating cone is firmly plugged in the tubeway.

For use of the instrument as per second embodiment, when the knob made to slide towards the IUD end causes the carriage to also move the string is then unwrapped from over the hook and the floating plug gets plugged out, and the string is in the unlocked or the released condition.

In yet another embodiment, the string management comprises an extended receptacle with an open side on the operator side of the carriage, and an end plug with a slit integratedly provided on the operator end of the base.

In the instrument as per third embodiment that is ready to use, the string emerges out of the extended receptacle, taut, sits on the slit, and emerges out of an opening of the base while the extended receptacle is firmly mounted on the end plug, keeping the string in the locked condition.

For use of the instrument as per third embodiment, when the operating knob causes the carriage to also move towards the IUD end, the extended receptacle gets dismounted from the end plug, string is untrapped from an in-between of the end plug and the extended receptacle, and thus the string is in the unlocked or the released condition.

There is provided at least one outpoint and one inpoint on the floor of the base. The outpoint and the inpoint is essentially a tapered hole. The string exits from the outpoint and re-enters from the inpoint. The string is accessible to the medical service provider between the outpoint and the inpoint and the medical service provider has a preferred option to trim the string as per sounding measurement of uterus of woman, BEFORE inserting the graduated tube in the cervix thereby avoiding use of scissors or cutting tool inside vaginal cavity. The outpoint is at a trim length which is a minimum recommended excess string length expected to be hanging outside cervical os in vaginal cavity of woman. The inpoint is at a conservative length. Medical service provider has the freedom to trim the string anywhere within the conservative length. A scale is provided alongside to facilitate precision in trimming.

When the medical service provider uses the option of trimming the string before insertion, the method to load the instrument and safely place the IUD in uterus with above variations comprises the steps of:

a) Sounding a uterus of woman and determining a uterine depth,
b) Sliding the operating knob towards an IUD end till the arms of the IUD are folded and fully contained in the graduated tube,
c) Sliding the operating knob further towards the IUD end till the graduated tube projects out by a length of the uterine depth, judging by hearing an audible clicking sound produced due to the pair of locking tooth negotiating with the array of inclines and notches or judging by the measurement markings on the graduated tube aligning with the flange or by the position of the pointer of the operating knob at the knob markings on the cover,
d) Trimming an excess length of the strings of the IUD anywhere in the conservative length,
e) Inserting the graduated tube in the uterus till the flange touches cervical os of the uterus,
f) Sliding back the operating knob till the dynamic stopper retracts by the sliding length and stops,
g) Further inserting the graduated tube in the uterus till the flange of retracted dynamic stopper again touches the cervical os,
h) Sliding back the operating knob as much as possible, and
i) Taking out the graduated tube from woman.

As another variation, the base has an out opening through which the string is still available to the medical service provider. The medical service provider can exercise the option to manually load the IUD if that suits the service provider as per his or her previous experience or convenience.

As yet another variation the push rod has a longitudinal channel or an equivalent construction to protect and shield the string from getting entangled in the graduated tube.

The instrument operates from its either side, whether curvature up or curvature down, while maintaining a horizontal orientation.

BRIEF DESCRIPTION OF DRAWINGS

FIG. 6 is a perspective view of a cover while
FIG. 8 are two perspective views of a carriage while
FIG. 12 is a sectional view of a first embodiment of a string management arrangement with a string unlocked, while
FIGS. 19 and 19A is a sectional view of a second embodiment of the string management arrangement with the string locked,
FIG. 19A is a sectional view with the string unlocked, while
FIGS. 20, 20A and 20B, are views showing string trimming arrangement after loading but before insertion of IUD, while
FIGS. 21, 21A are perspective views of the base and the carriage, while

DETAILED DESCRIPTION OF INVENTION

The present invention of an instrument to load and insert an upfoldable intra-uterine device and process thereof will now be described with reference to the accompanying drawings. It is to be understood that the description explains the preferred embodiments and several ways are possible around the invention. Apropos, the description should not be construed to limit the invention in any way whatsoever. The terms and expressions which have been used here are merely for description and not for limitation. The term "preparing" and "loading" are used interchangeably.

Figure 1:
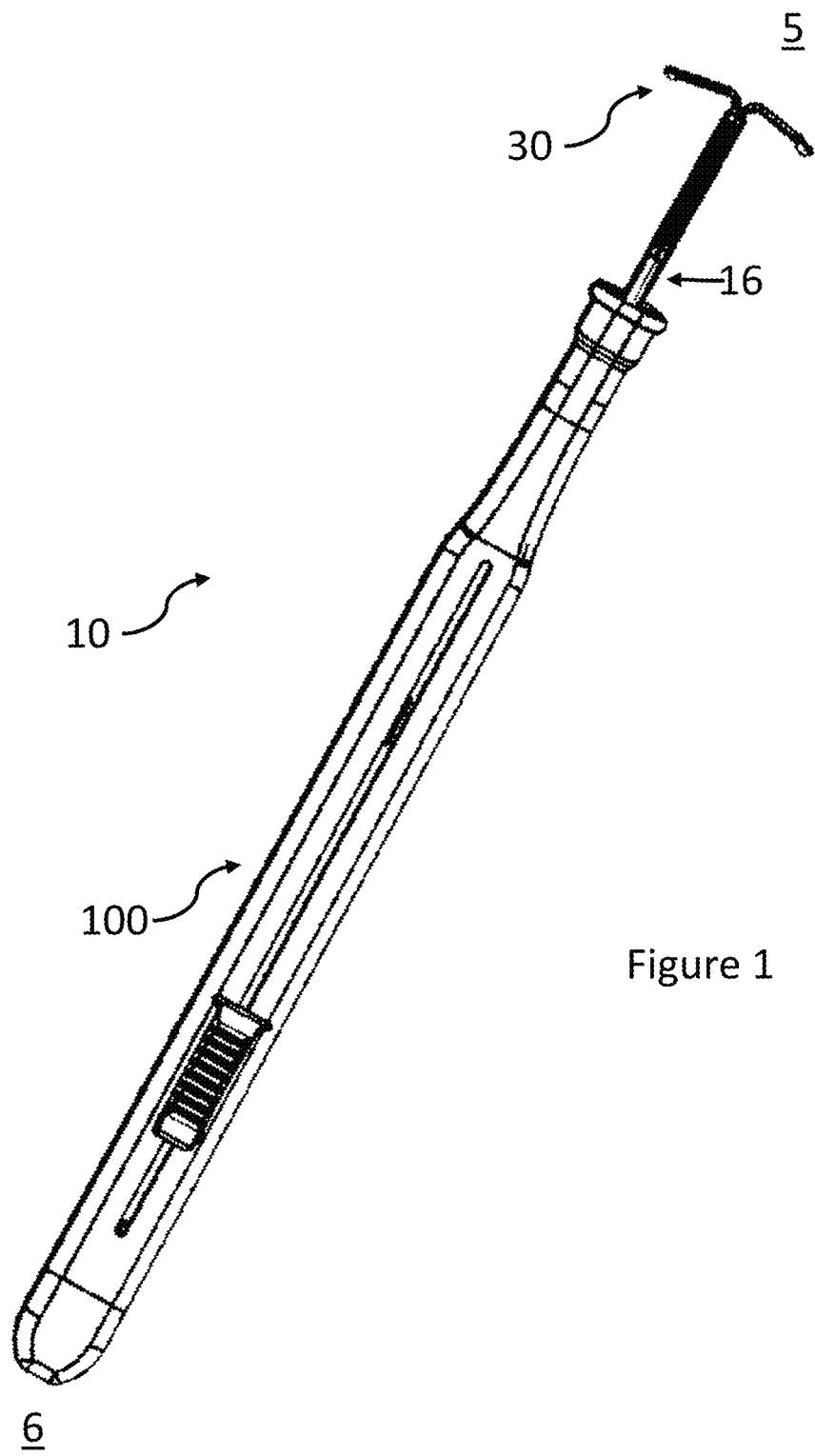
FIG. 1 is a perspective view of an instrument as per present invention.
Figure 3:
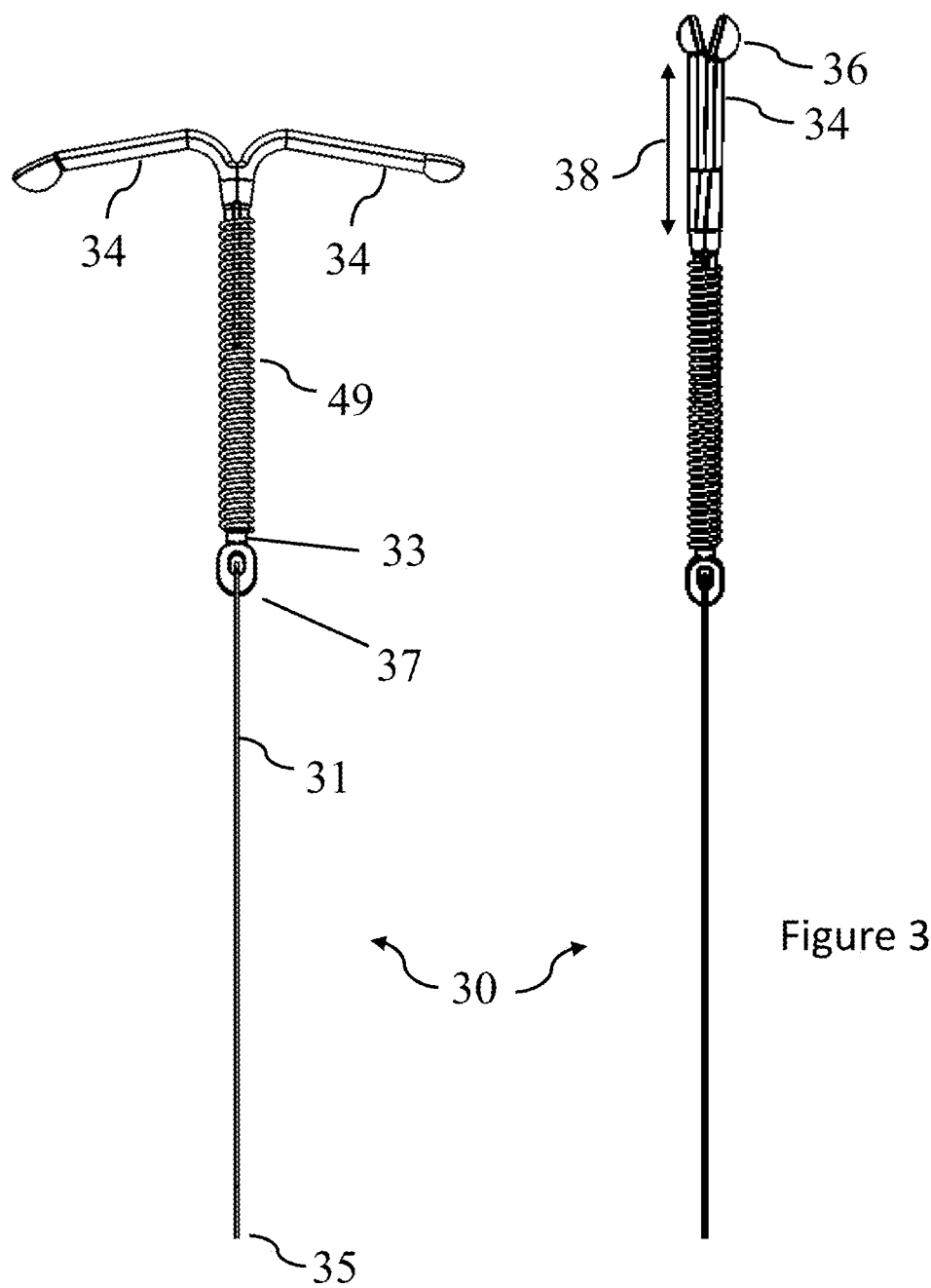
FIG. 3 are front views of an IUD with its arms unfolded (almost horizontal) and folded (almost vertical).
Figure 12:
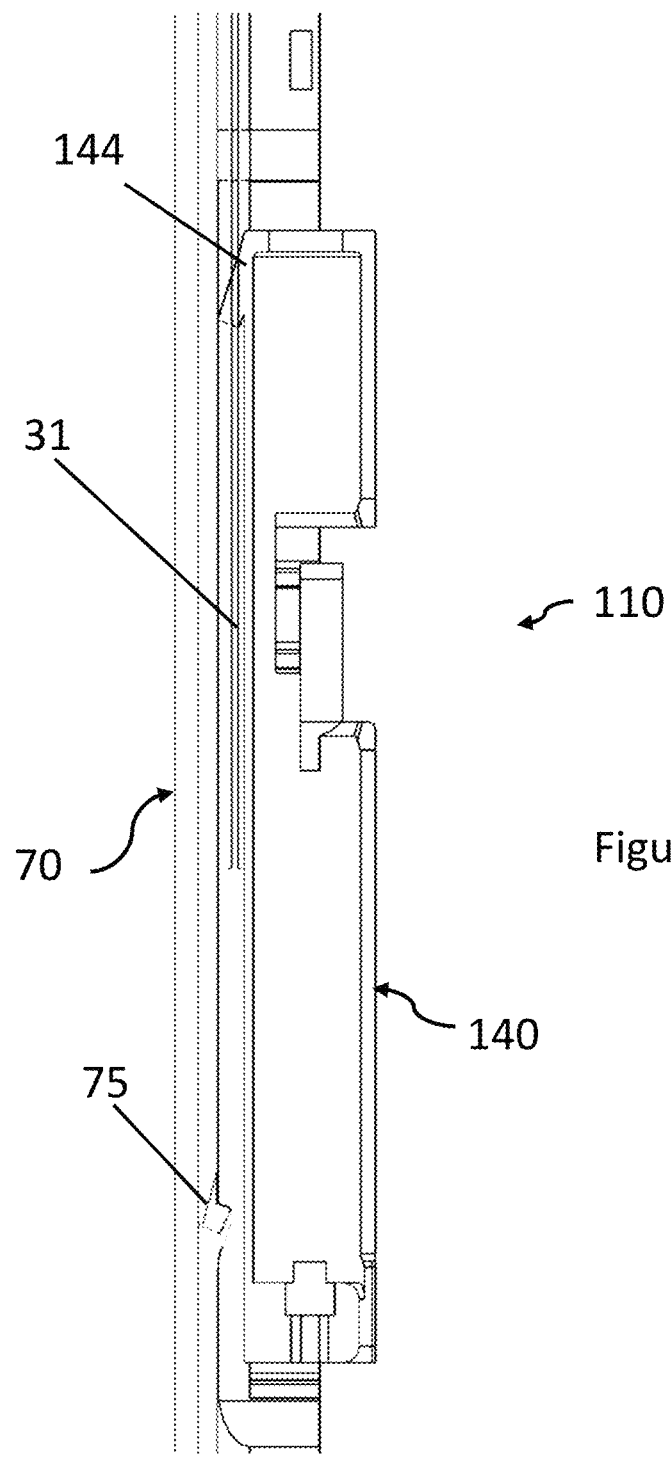
Figure 12A:
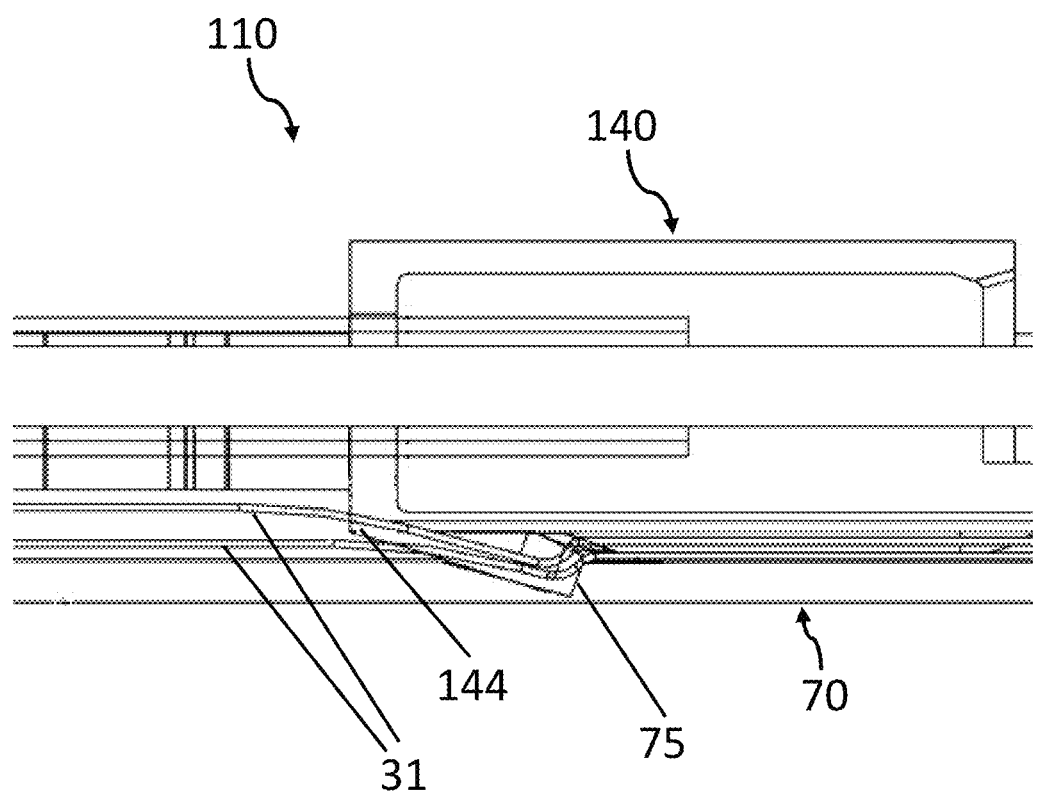
FIG. 12A is a sectional view showing the string locked.
Figure 13:
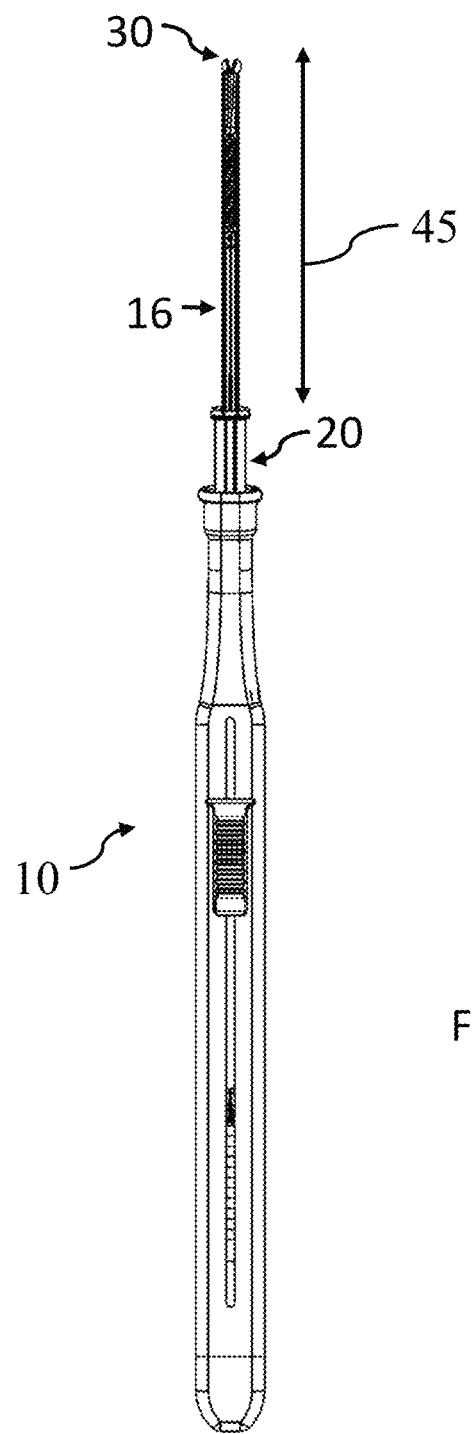
FIG. 13 is a front view of the instrument with the graduated tube extended in accordance with uterine depth of uterus.
Figure 14:
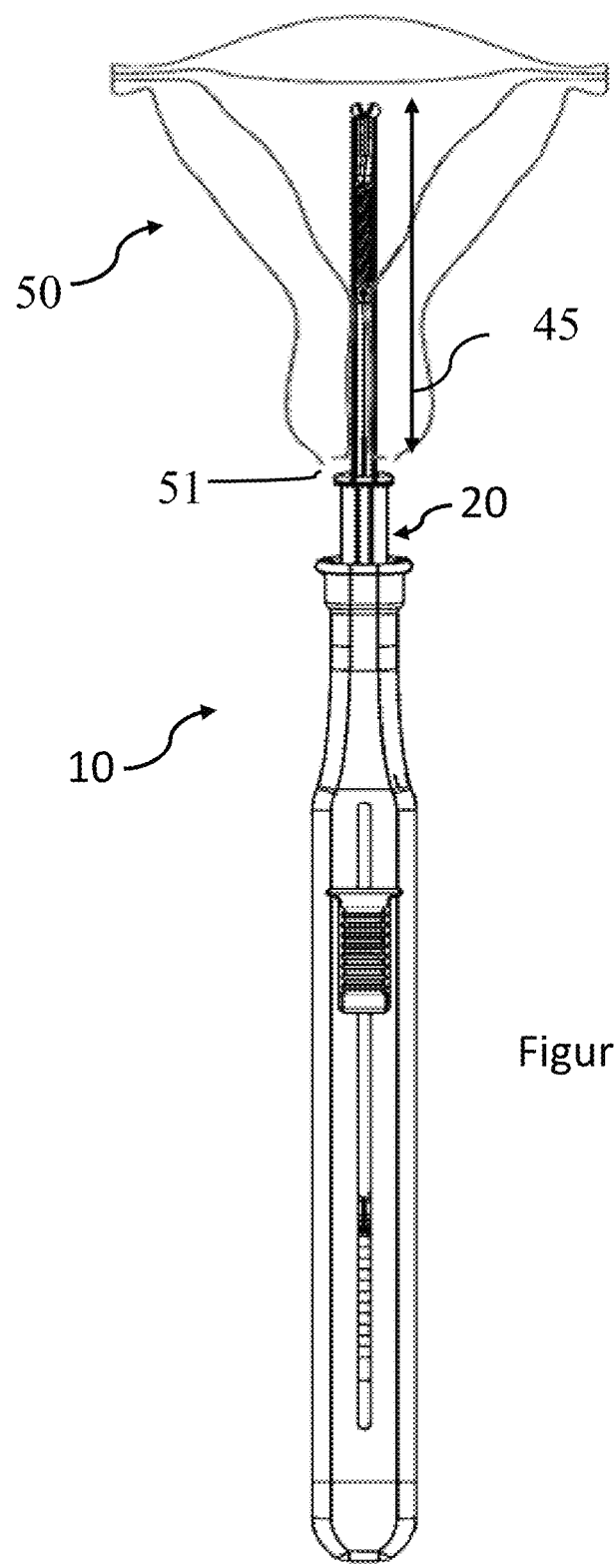
FIGS. 14 to 18 are front views of steps of insertion and safe release of the IUD in uterus.
Figure 15:
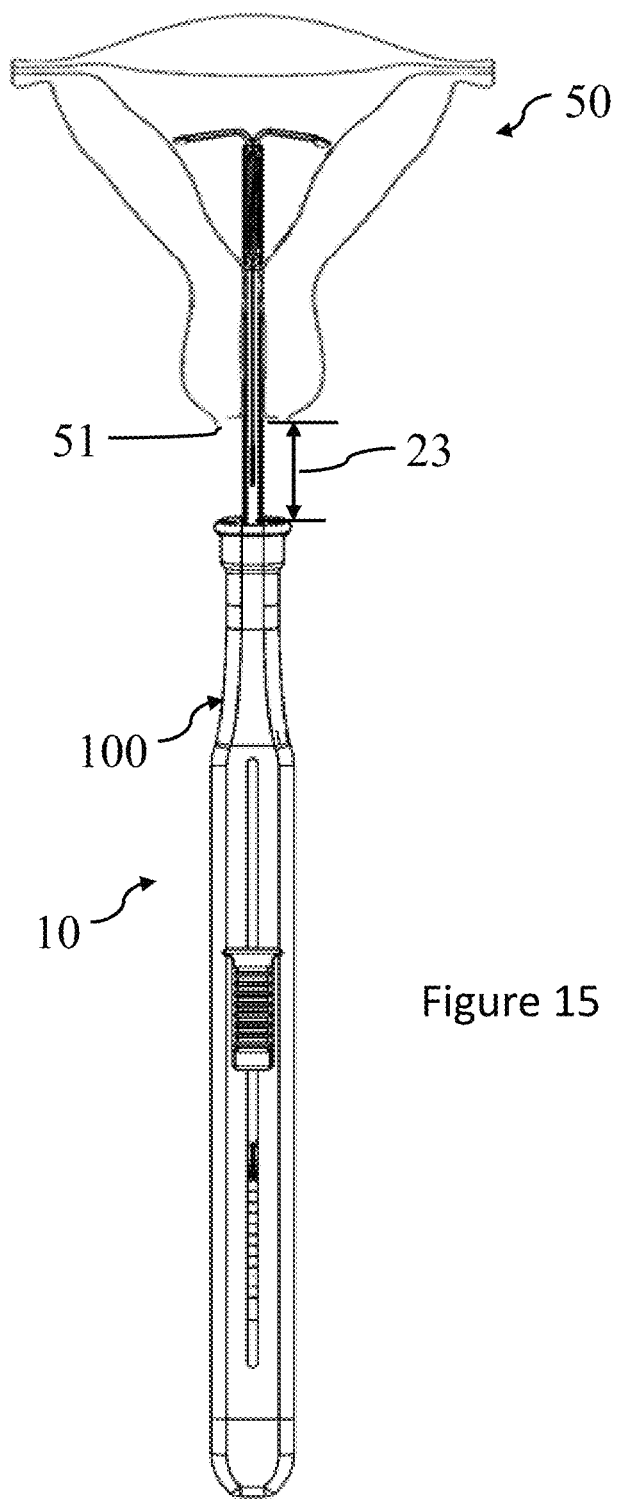
Figure 16:
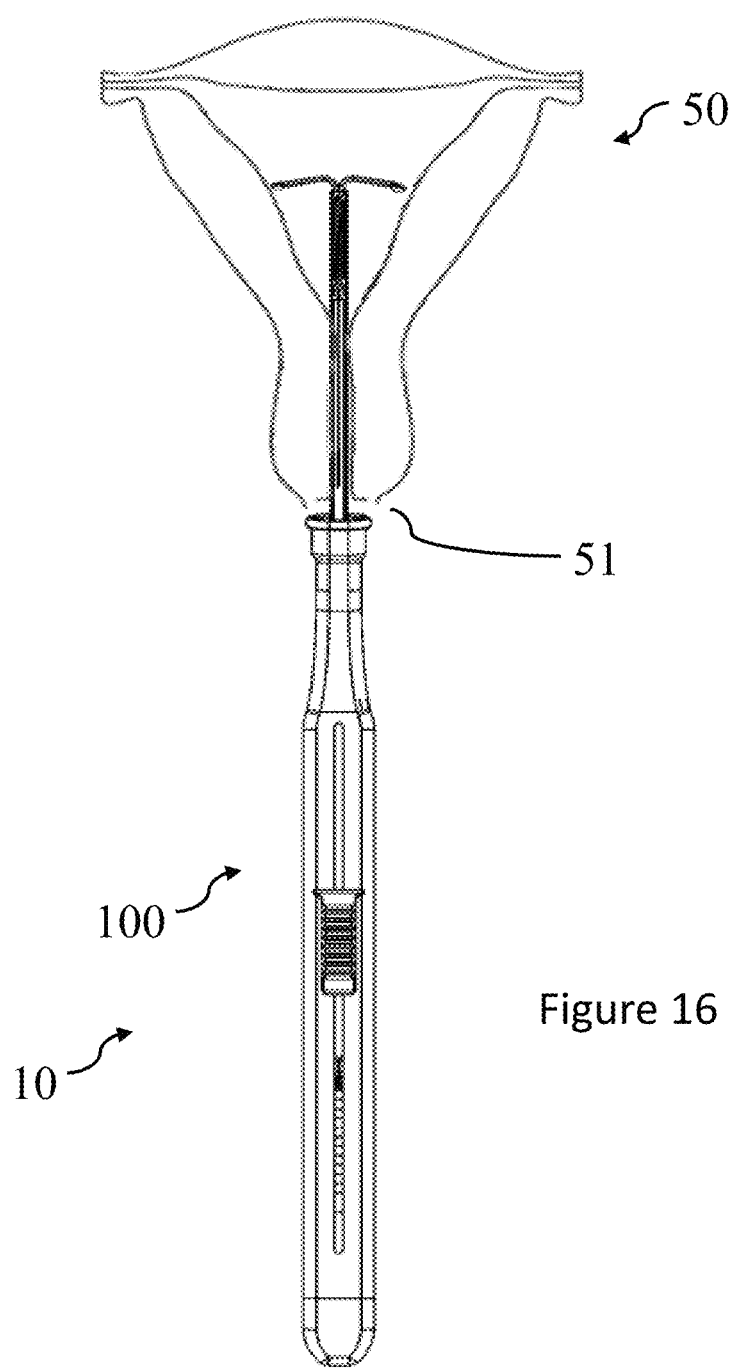
Figure 17:
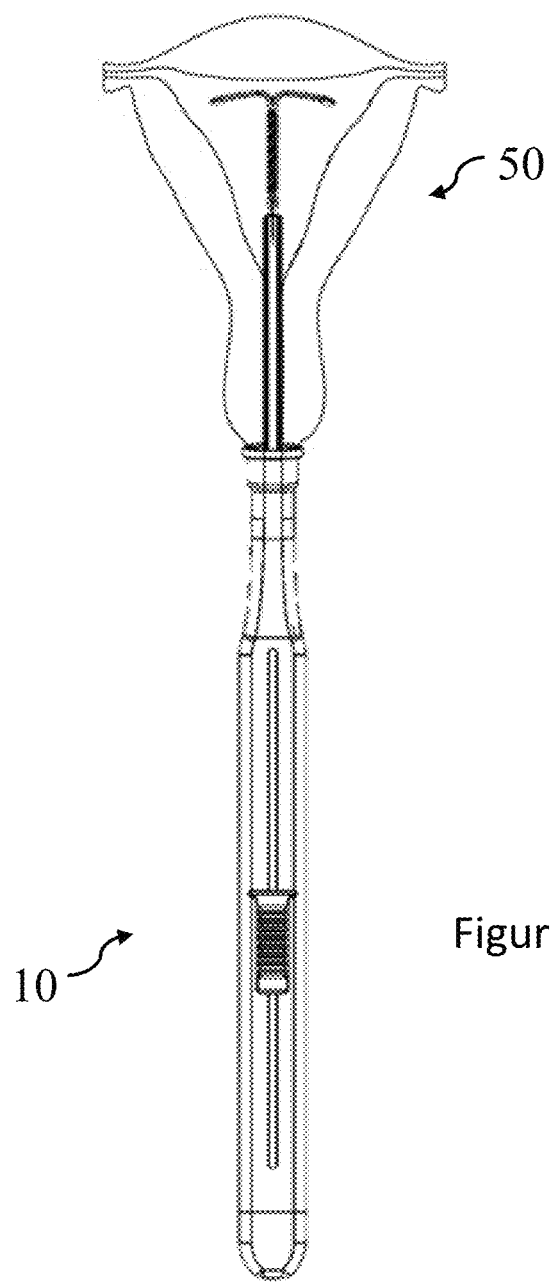
Figure 18:
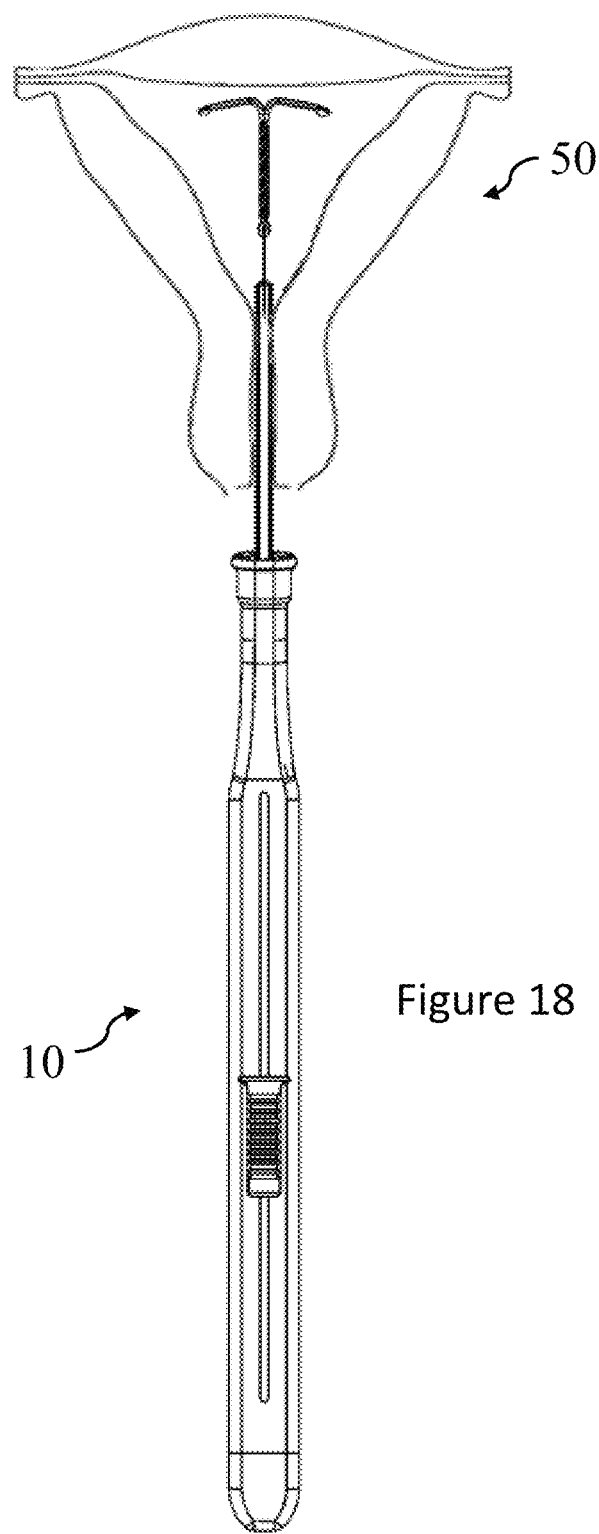
Figure 19A:
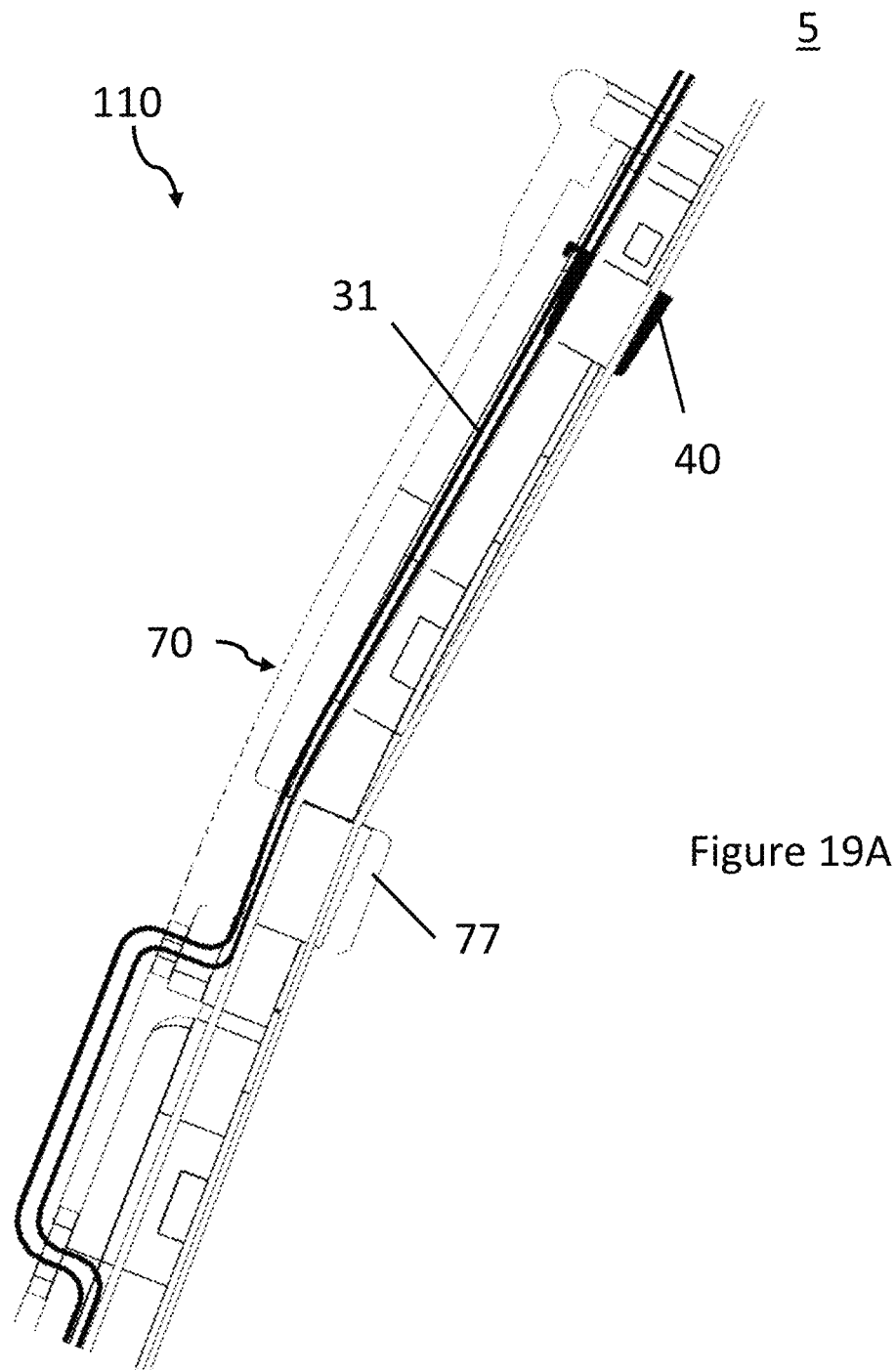
Figure 19B:
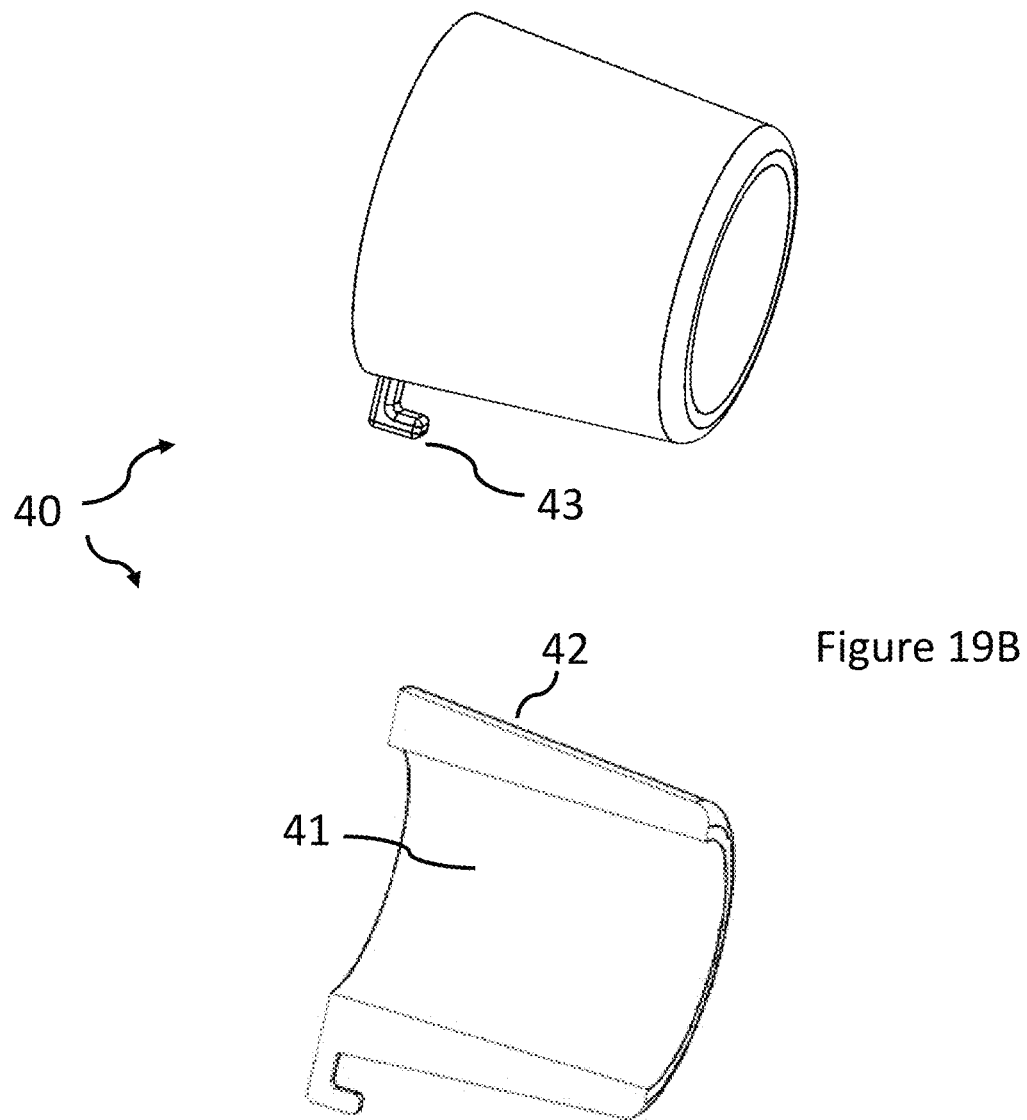
FIG. 19B is a perspective view and a sectional view of a floating cone.
Figure 20:
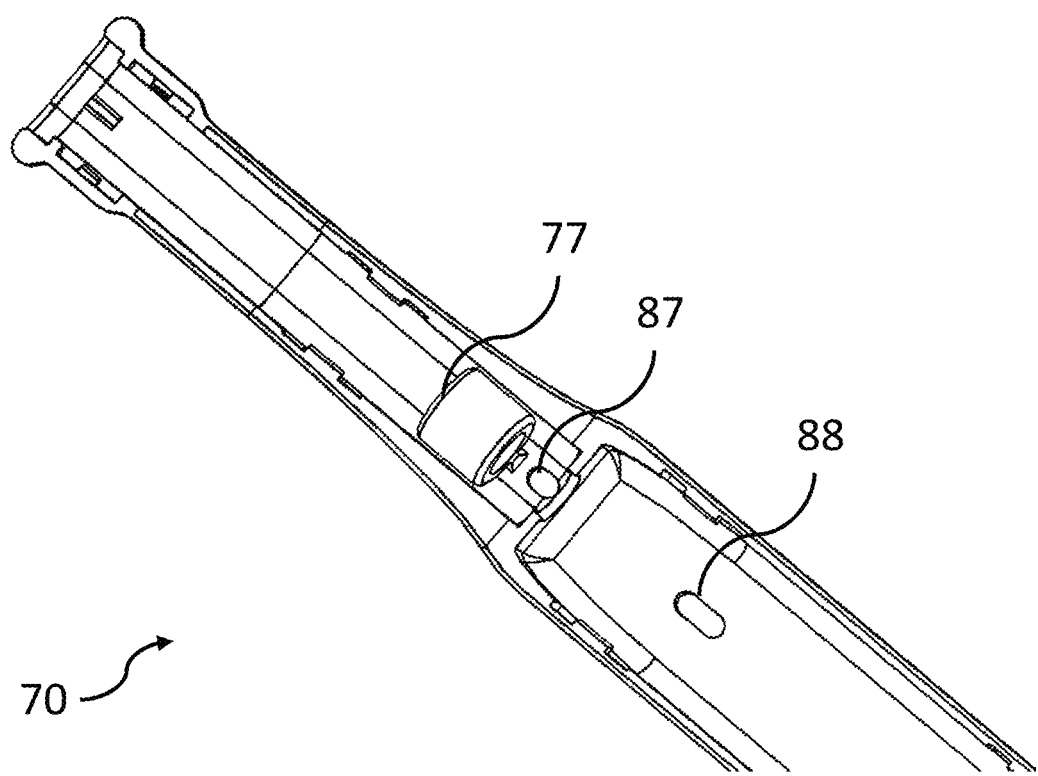
Figure 20A:
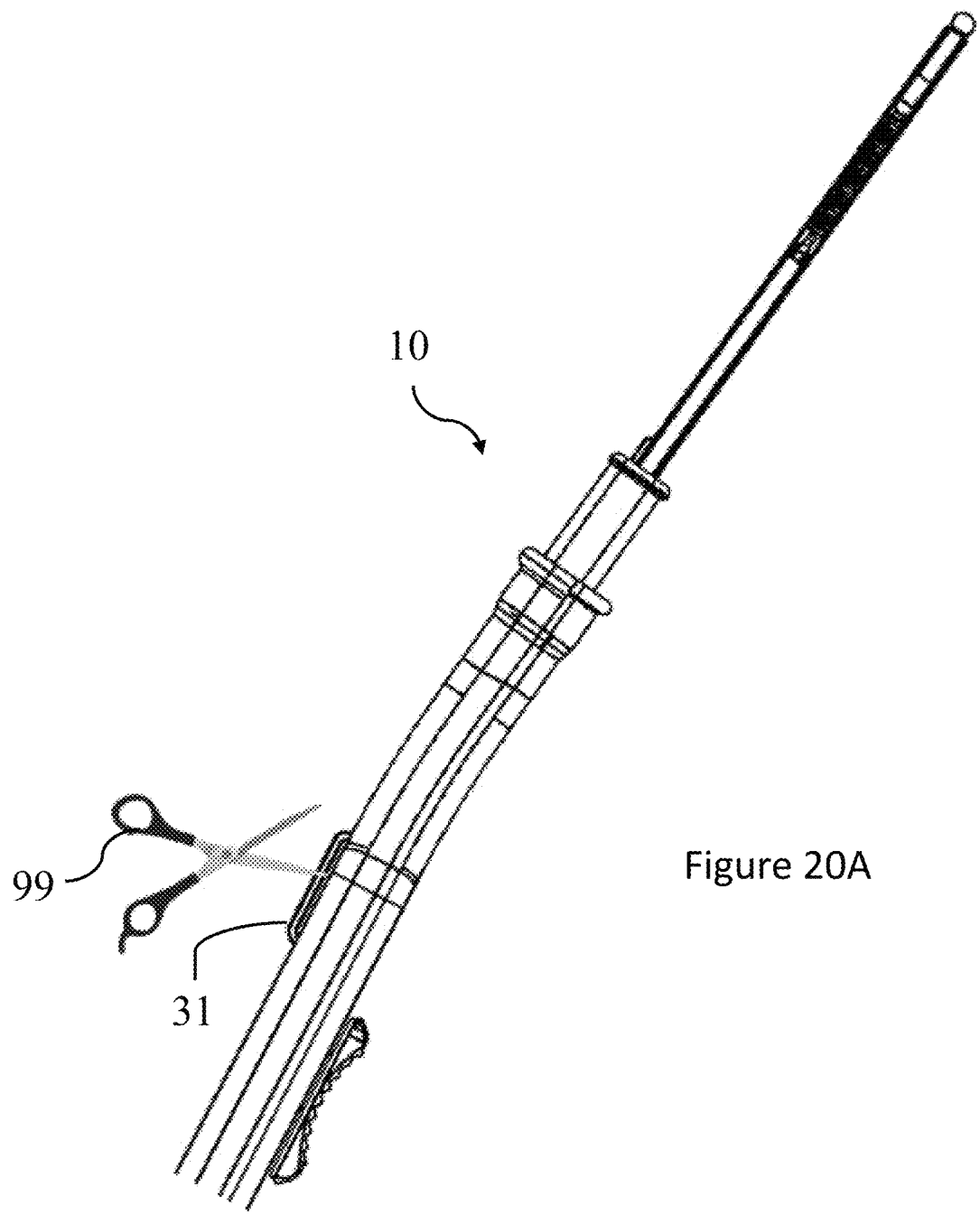
Figure 20B:
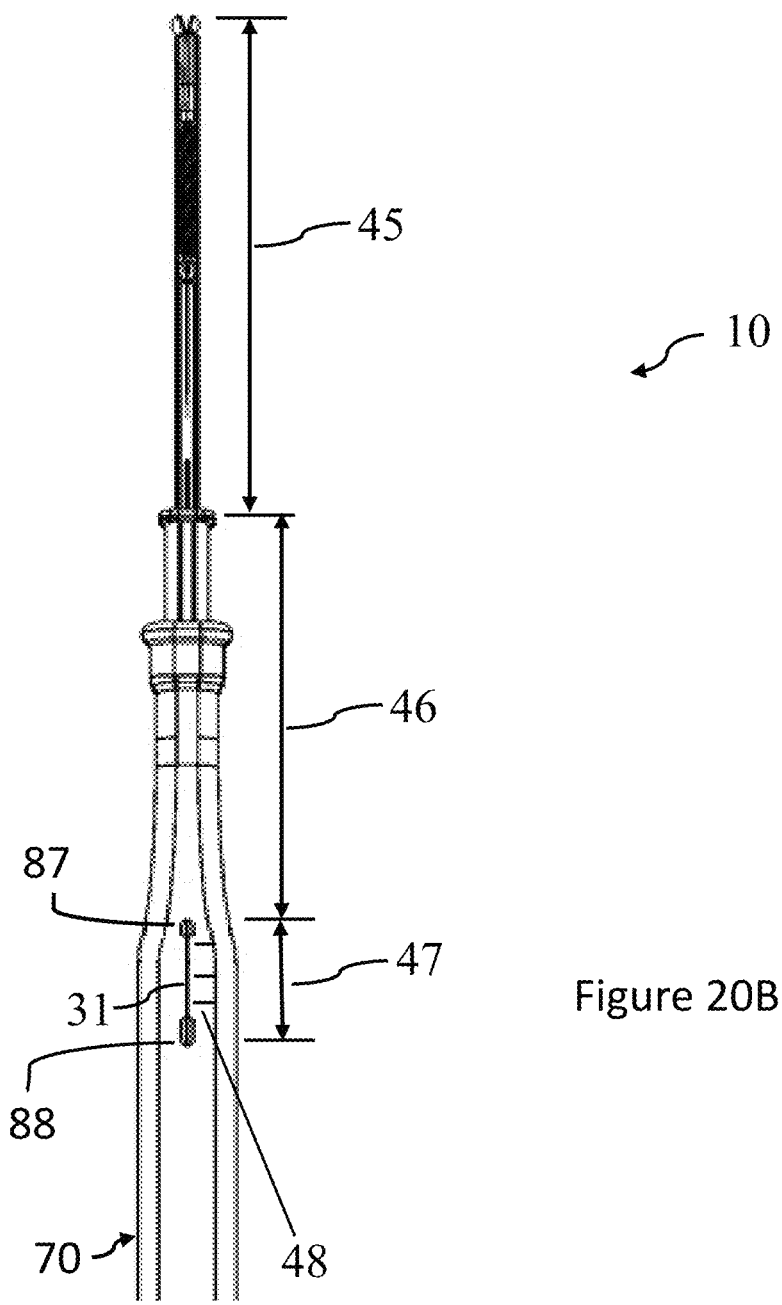
Figure 20C:
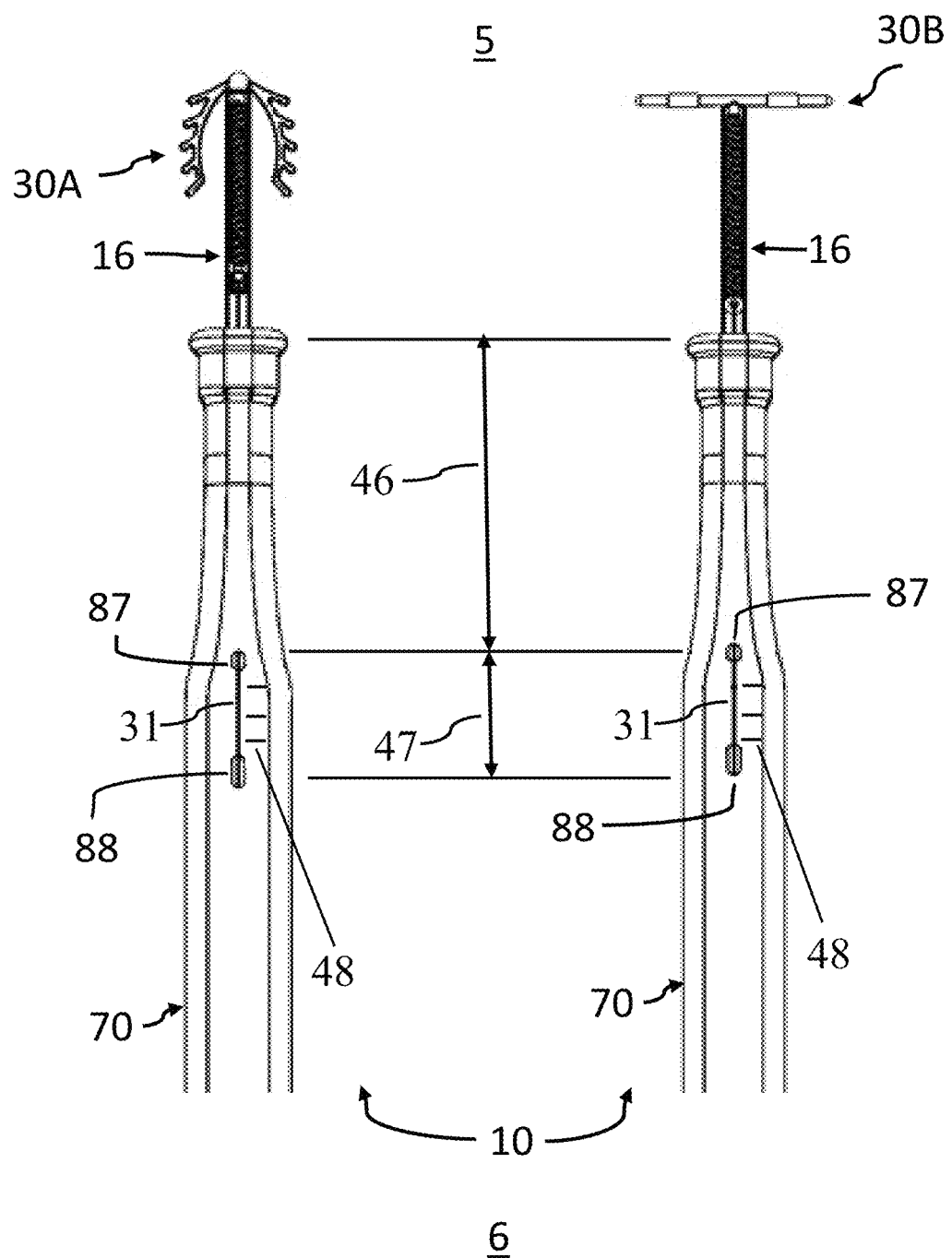
FIG. 20C shows string trimming arrangement for different kinds of IUDs.

FIG. 1, 2 the instrument (10) according to present invention comprises a "T" shaped intra-uterine device (30), a graduated tube (16), a push rod (17) inside the graduated tube (16), a dynamic stopper (20) with a flange (25), operated by an operating device (100). The instrument (10) further comprises a string management arrangement (110), shown in FIGS. 12 and 12A being one of the embodiments. The preferred embodiment is around the IUD (30) generally comprising a frame having two arms (34) and a stem (33), with both arms (34) of the IUD (30) foldable away from the stem (33) of the IUD (30), as shown in FIG. 3. The instrument (10) is shipped in this position when the IUD (30) is with its arms (34) in a "T" formation with respect to the stem (33), as it should be when placed in uterus of woman. The IUD (30) further comprises a contraceptive material (49) disposed around the stem (33), and at least one string (31) emerges from a lower end (37) of the stem (33). The string (31) has a terminating ends (35). The string (31) of the IUD (30) is in an unreleased or a locked condition, and taut between the lower end (37) and the operating arrangement (110), when the instrument (10) is received by a medical service provider. In the present invention, the string (31) is NOT required to be pulled/manipulated by the medical service provider for loading or preparing the instrument (10), and the loading/preparing method is described below. Apropos, the terminating ends (35) of the string (31) can be concealed in the operating device (100) and may or may not be visible/accessible to medical service provider.

As shall be evident, the process of loading, inserting in uterus and safely releasing the IUD (30) is carried out by a single hand operation, and it is of great benefit to the medical service provider. An IUD end (5) and an operator end (6)

signifies direction of the instrument (10) and all parts while describing features, sub-assembly, assembly and method of use.

Figure 4:
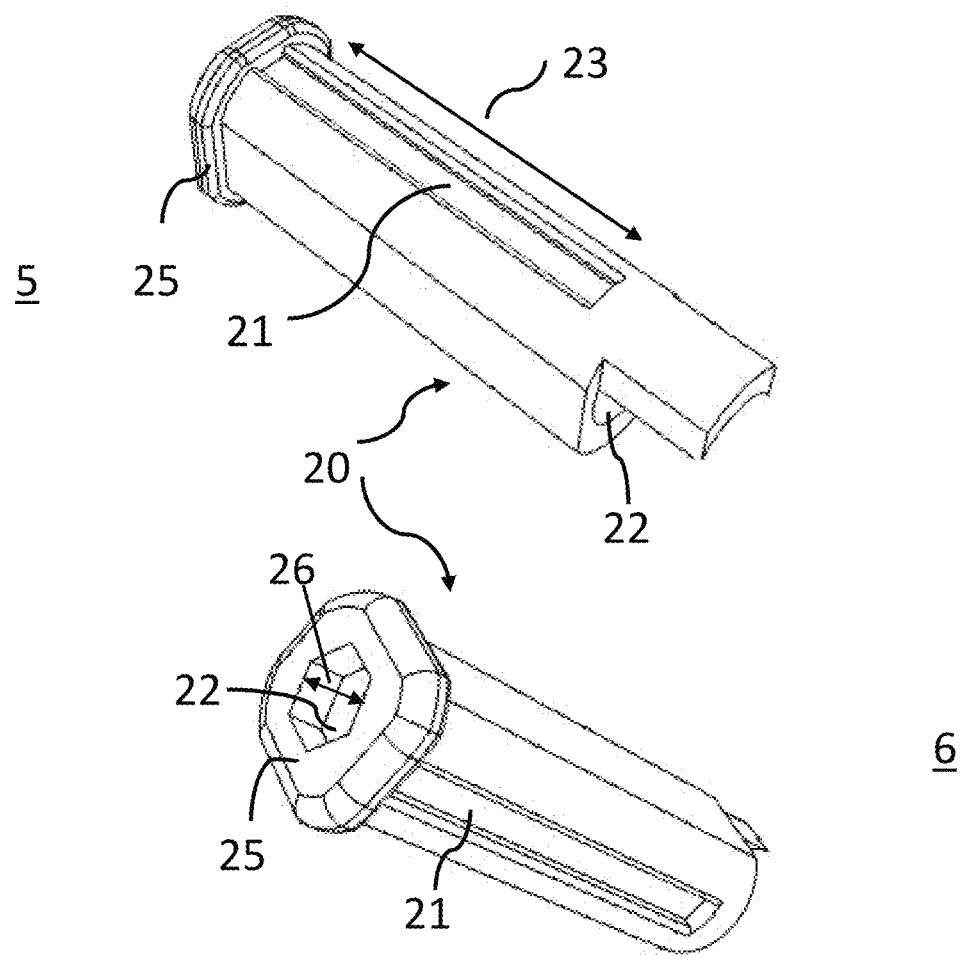
FIG. 4 are perspective views of a dynamic stopper.

FIG. 4, the dynamic stopper (20) is a tubular channel (22) having the flange (25) at the IUD end (5) of the dynamic stopper (20) and a non-circular outer face of lesser mating perimeter than that of the flange (25). There are provided guide paths (21) at least on two alternate faces of the dynamic stopper (20). A sliding length (23) of the dynamic stopper (20) is commensurate with an arm length (38) of the arms (34) of the IUD (30). A face distance (26) of the regular hexagonal channel (22) permits multi-point contacts on the graduated tube (16) and allows a passage of the graduated tube (16) tightly.

Figure 2:
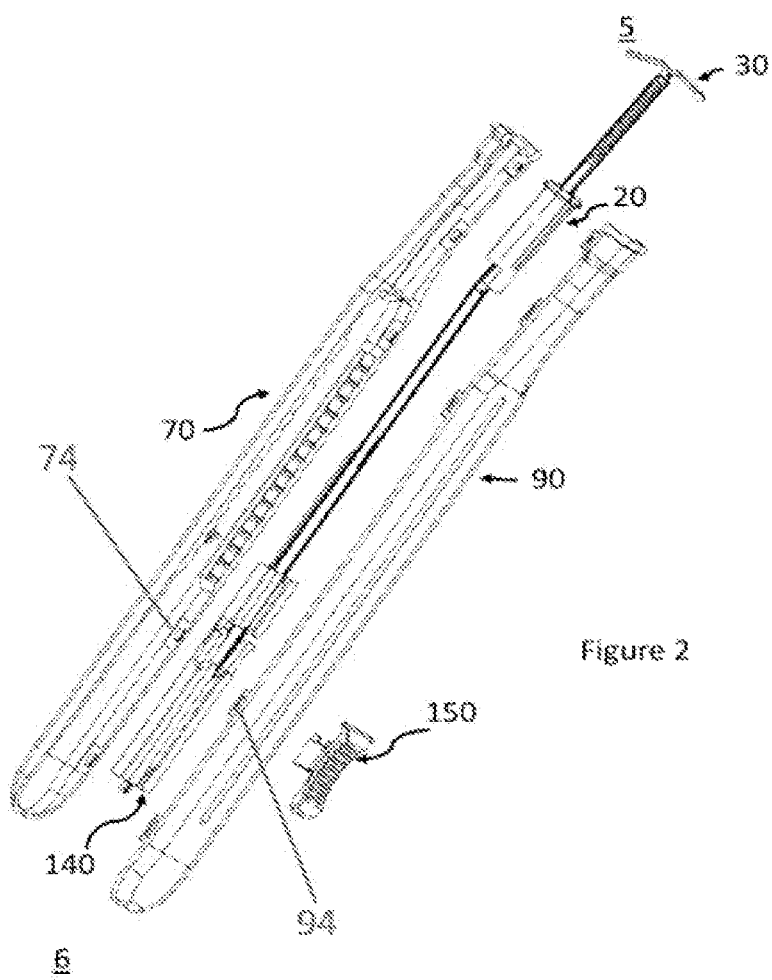
FIG. 2 is an exploded view of the present invention.

FIG. 2, the operating device (100) comprises
a base (70)
a cover (90)
an operating knob (150)
a carriage (140)

Figure 5:
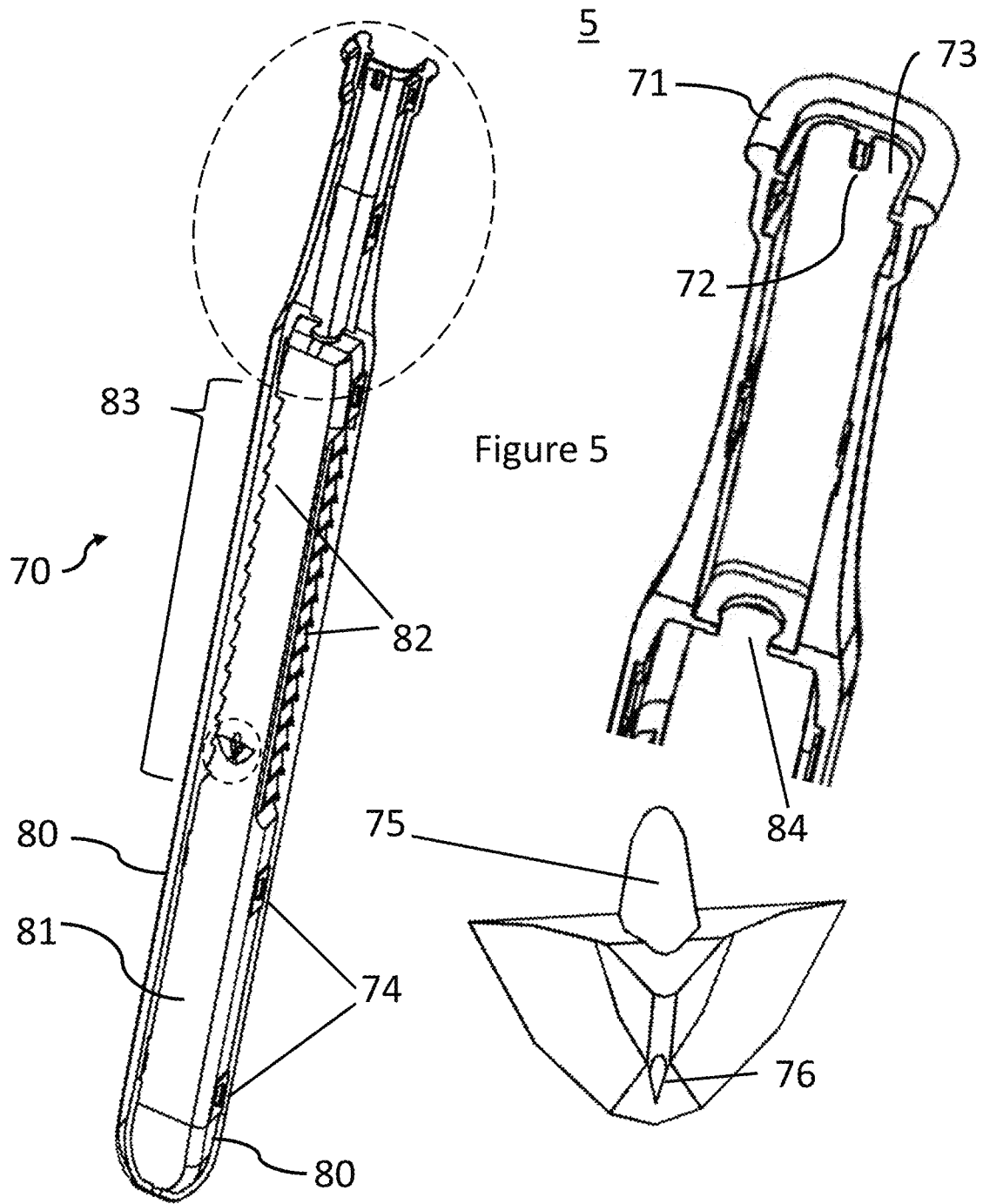
FIG. 5 is a perspective view of a base with enlarged views of encircled portion of the base.

FIG. 5, the base (70) has two parallel walls (80) a floor (81), an open neck construction (73) with a collar (71) and a first flange guiding projections (72) at its IUD end (5) of each wall (80) or on the floor (81). There are carrier guiding projections (73) on the floor (81).

On an inside of the walls (80) is provided an array of continuous incline and notches (82) alternately for a prescribed length (83). There are a plurality of cover engagement means (74) on the inside of both the walls (80). In the preferred embodiment, the cover engagement means (74) is a raised projection such as but not limited to a nub, dome, protuberance, etc. with surrounding material reduced to make room for a base engagement means (94).

The base engagement means (94) in the preferred embodiment is a receptacle, such as but not limited to an aperture, opening, window, etc., to commensurate with the raised projection, such that when the base (70) and cover (90) are pressed together, the raised projection is trapped in the corresponding receptacle. In another embodiment, the cover engagement means (74) can be a receptacle while the base engagement (94) means can be a raised projection. A tube guideway (84) is provided on the floor (81). Also provided is a string socket (75) with a hole (76). The base (70) is slightly curvatured.

Figure 8:
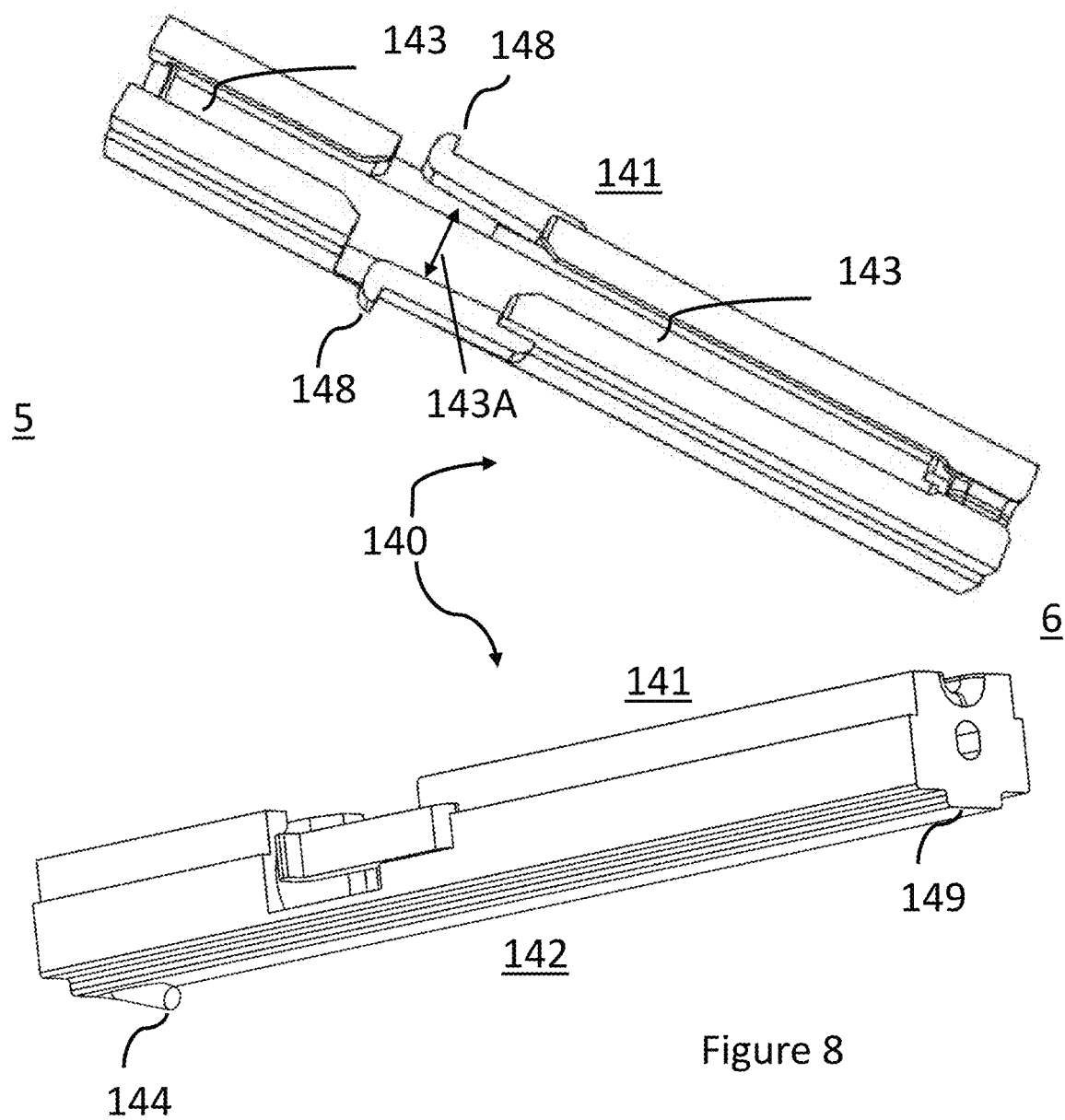
Figure 8A:
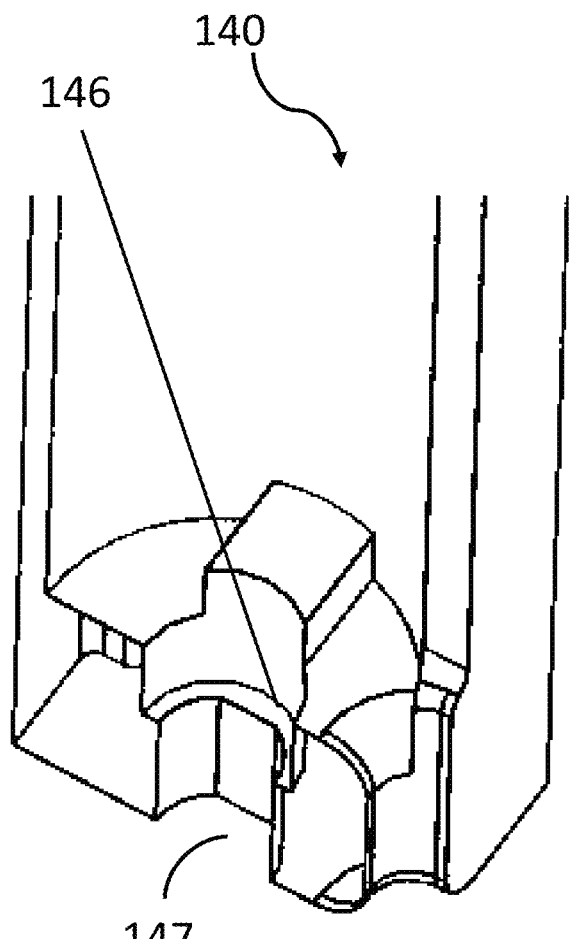
FIG. 8A is a partial sectional view of the carriage.

FIG. 8, 8A, the carriage (140) has a travel slot (143) on an upper side (141), at least a pair of locking tooth (148) on an either carrier side. The travel slot (143) has an assembly opening (143A) which is wider than the travel slot (143). On the lower side (142) is a travel surface (149). There is provided a string plug (144) on the lower side (142). At the operator end (6) is a pushrod passageway (147) with a seat (146).

Figure 7:
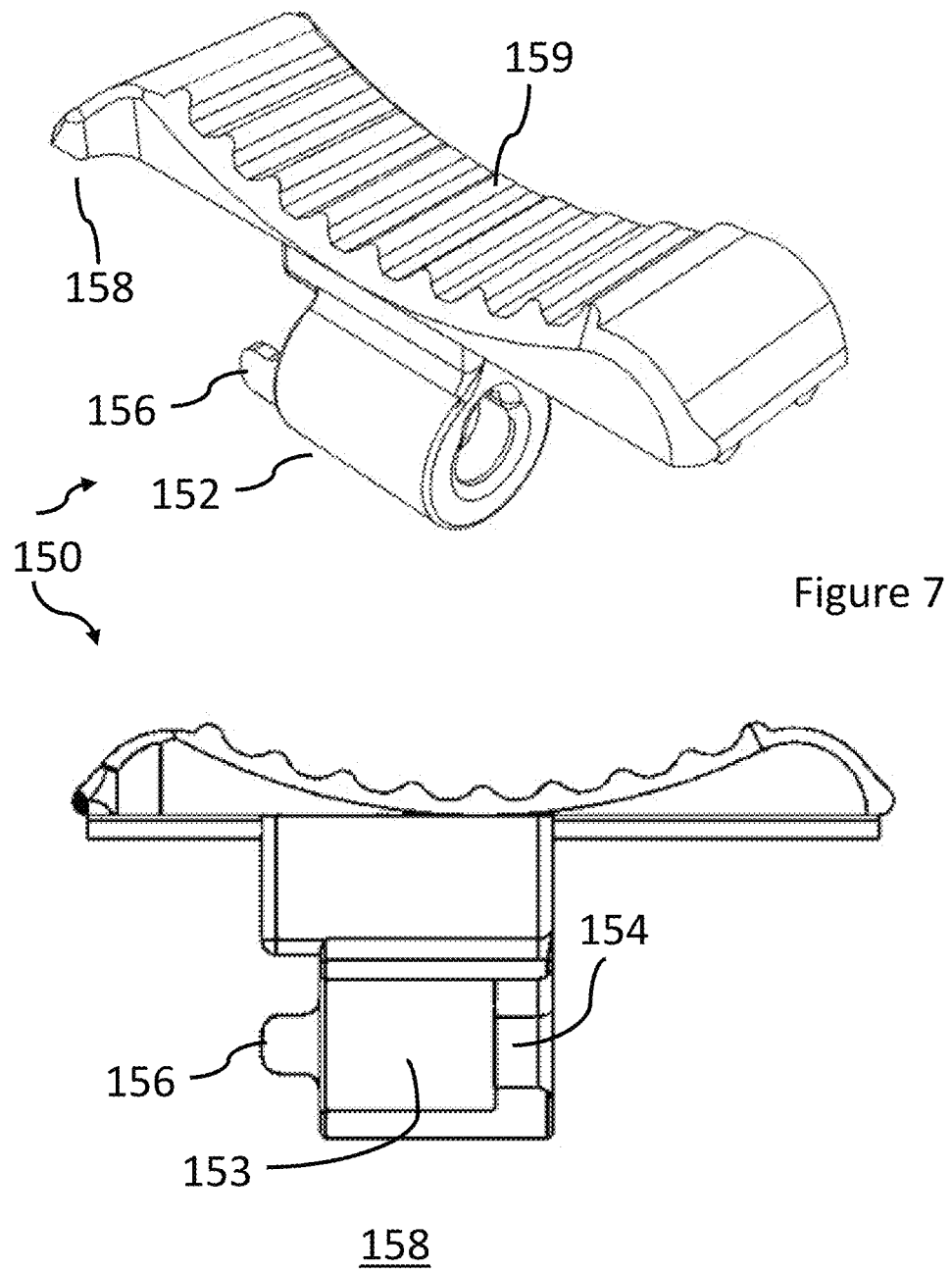
FIG. 7 is a perspective view and a sectional view of an operating knob.

FIG. 7, the operating knob (150) has a thumb surface (159), and at least a pointer (158) on an either knob side. There is provided a hanging tubular construction (152) on an opposite side (158) of the thumb surface (159). The tubular construction (152) has a larger diameter part (153) having a pair of pusher (156), and a smaller diameter part (154).

Figure 6:
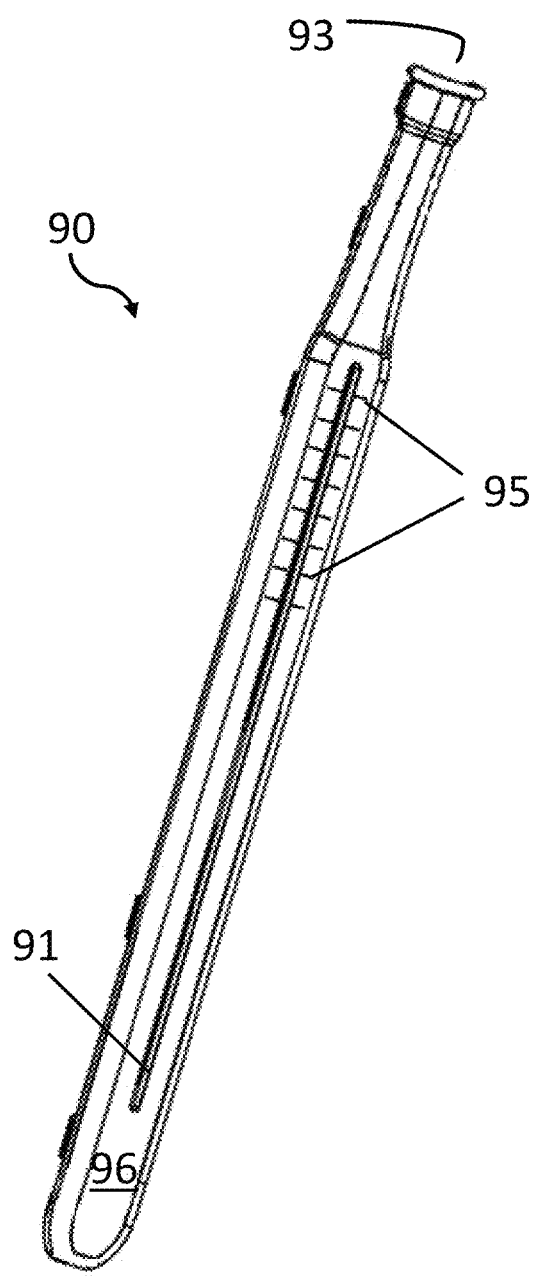
Figure 6A:
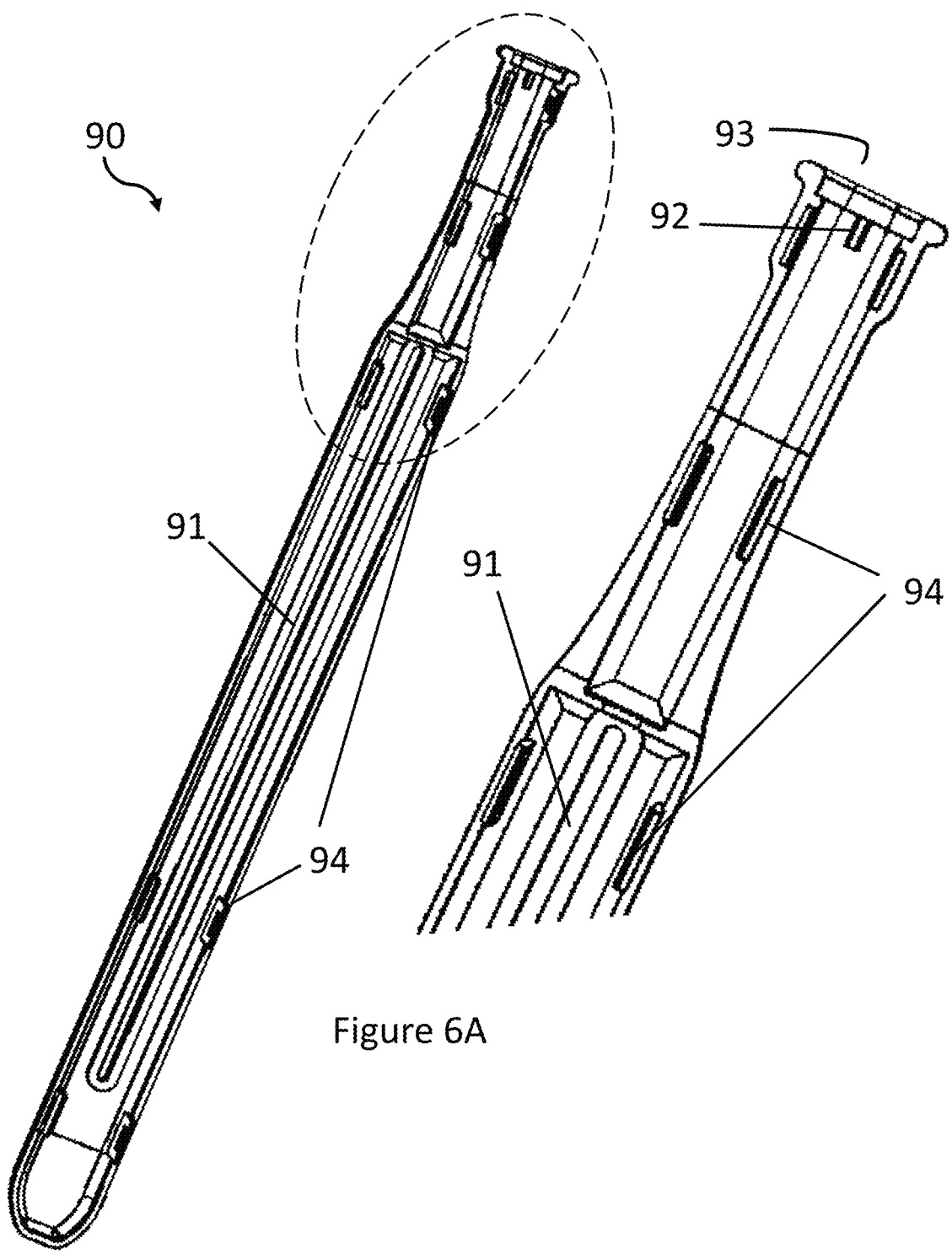
FIG. 6A is another perspective view with enlarged view of encircled portion of the cover.

FIG. 6, 6A, the cover (90) has a slot (91), an open complementing neck construction (93), a second flange guiding projections (92), and a plurality of base engagement means (94) equal in number of the cover engagement means (74). A knob markings (95) are provided on an external side (96) of the cover (90). The cover (90) is slightly curvature in accordance with the base (70).

The reversible collapsible means (19) comprises a pair of arms (19A) and (19B), separated by a slit (19C). When the reversible collapsible means (19) is pushed in the pushrod passageway (147), ends of the respective arms (19A, 19B) come closer temporarily, and separate again as the collar (18) sits in the seat (146).

Figure 9:
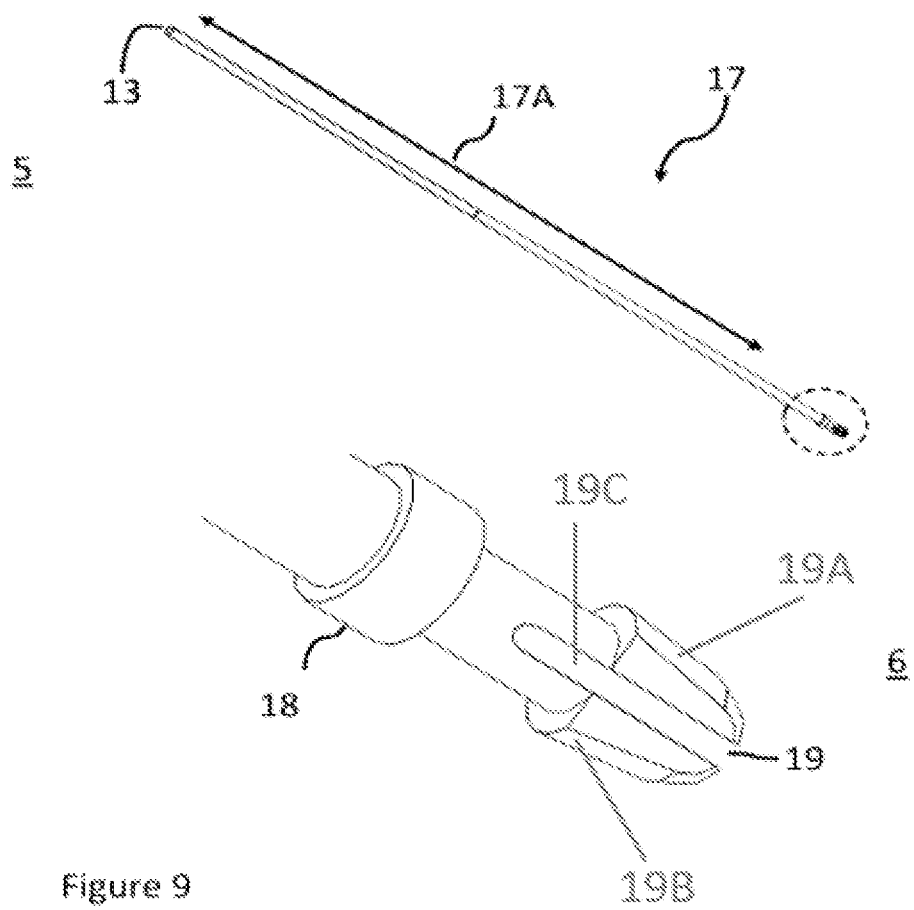
FIG. 9 is a perspective view of a push rod with an enlarged view of its encircled portion.

FIG. 9, the pushrod (17) is a slender cylinder, has a collar (18), a reversibly collapsible fitment means (19) at its operator end (6) and a flat surface (13) at the IUD end (5).

Figure 10:
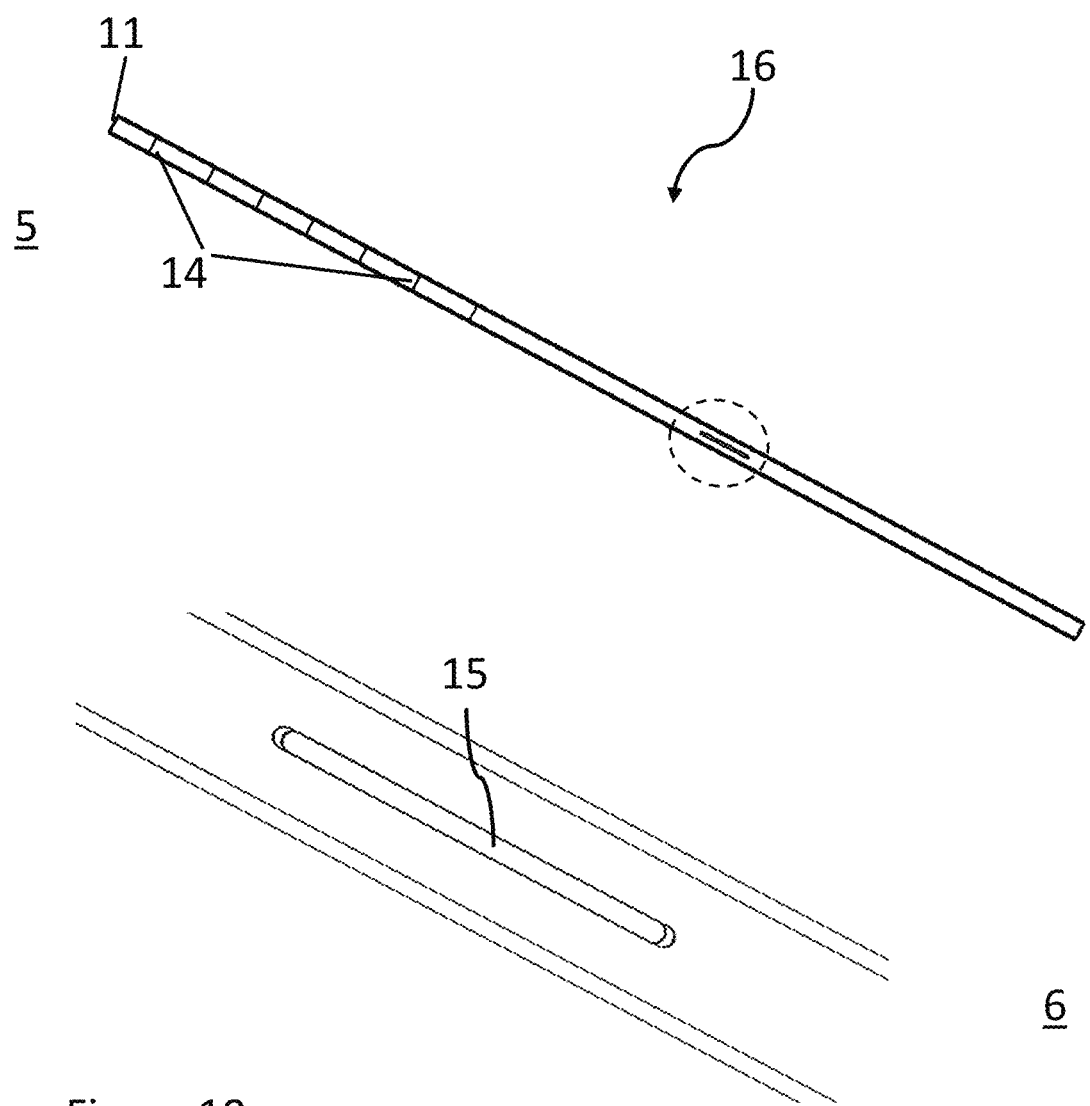
FIG. 10 is a perspective view of a graduated tube with an enlarged view of its encircled portion.

FIG. 10, the graduated tube (16) is a thin walled hollow cylinder having an edge (11) at the IUD end (5), a measurement markings (14) and a string exit slot (15).

Figure 11:
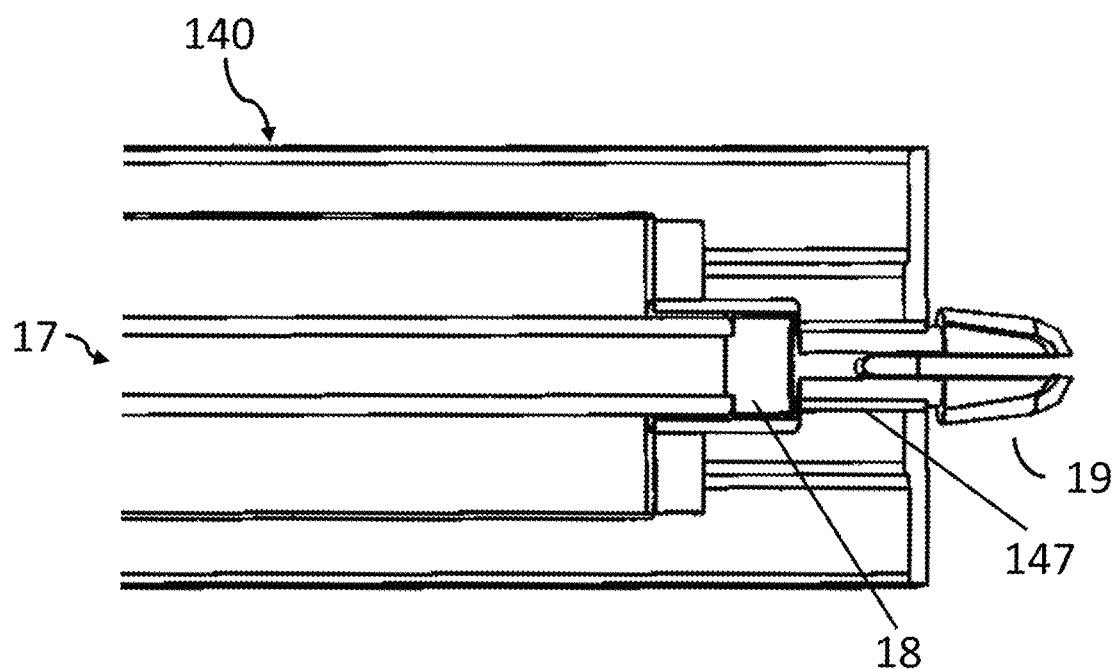
FIG. 11 is a partial sectional side view of the carriage and the push rod engaged therein.

In the instrument (10) that is ready to use, the dynamic stopper (20) slidably resides in the base (70) free to slide along the guide paths (21) constrained by the first flange guiding projections (72) and or the second flange guiding projections (92), and can slide by the sliding length (23). The operator end (6) of the graduated tube (16) is slided with a little force through the tubular channel (22) of the dynamic stopper (20), till the operator end (6) of the graduated tube (16) is disposed firmly in the larger diameter part (153) of the knob (150). The dynamic stopper (20) rides on the graduated tube (16). The hanging tubular construction (152) of knob (150) resides in the travel slot (143) of the carriage (140). The push rod (17) largely resides inside the graduated tube (16) with the reversible collapsible fitment means (19) of the pushrod (17) pushed in the pushrod passageway (147) such that the collar (18) of the pushrod (17) sits in the seat (146) of the carriage (140), FIG. 11. The stem (33) of the IUD (30) sits in the graduated tube (16) at its IUD end (5), while the string (31) is slipped in and exits from the string exit slot (15) and is trapped between the string plug (144) and the string socket (75) while keeping it tautly pulled out from the hole (76), thus the string (31) is in the unreleased or the locked condition, FIG. 12. The terminating ends (35) of the string (31) are contained inside of the base (70) near its operator end (6).

For use of the instrument (10), when the knob (150) is made to slide towards the IUD end (5), the graduated tube (16) and the dynamic stopper (20) also travel towards the IUD end (5). The dynamic stopper (20) travels forward by the sliding length (23) while the graduated tube (16) engulfs the arms of the IUD (30) till the edge (11) of the graduated tube (16) is stopped by the dome shaped ends (36) of the arms (34) having come almost together. Further sliding of the knob (150) towards the IUD end (5) causes the carriage (140) to also move towards the IUD end (5) due to the pusher (156) of the knob (150), and consequently the pushrod (17) also correspondingly moves. A movement of the carriage (140) towards the IUD end (5) causes the string plug (144) to move away and thus unplug from the string socket (75) and the string (31) is in an unlocked or a released condition, FIG. 12A.

The string management arrangement (110) in this embodiment therefore comprises the string plug (144) of the carriage (140) and the string socket (75) of the base (70); and locking and unlocking the string (31) takes place as described above.

FIGS. 13-18, a method to load the instrument (10) and safely place the IUD (30) in uterus (50) comprises the steps of:
a) Sounding a uterus of woman and determining a uterine depth (45)
b) Sliding the operating knob (150) towards an IUD end (5) till the arms (34) of the IUD (30) are folded and fully contained in the graduated tube (16),
c) Sliding the operating knob (150) further towards the IUD end (5) till the graduated tube (16) projects out by a length of the uterine depth (45), judging by hearing an audible clicking sound produced due to the pair of locking tooth (148) negotiating with the array of inclines and notches (82) or judging by the measurement markings (14) on the graduated tube (16) aligning with the flange (25) or by the position of the pointer (158) of the operating knob (150) at the knob markings (95) on the cover (90), d) Inserting the graduated tube (16) in the uterus (50) till the flange (25) touches cervical os (51) of the uterus (50), e) Sliding back the operating knob (150) till the dynamic stopper (20) retracts by the sliding length (23) and stops, f) Further inserting the graduated tube (16) in the uterus (50) till the flange (25) of retracted dynamic stopper (20) again touches the cervical os (51)

g) Sliding back the operating knob (150) as much as possible, h) Taking out the graduated tube (16) from woman, and i) Trimming an excess length of the strings (31) of the IUD (30).

Importantly, due to the inventive dynamic stopper (20) that moves equivalent to arm length (38), the medical service provider doesn't have to approximate intermediate stop and partial release of the IUD (30) as is prevalent in prior art products.

FIGS. 19, 19A, 19B, 20, in another embodiment, the string management (110) comprises a floating cone (40) floatingly disposed on the graduated tube (16) and a tubeway (77) integratedly provided on the base (70).

The floating cone (40) has a tubular hole (41) on an inside and a conical frustum (42) on an outside. There is provided a hook (43) on the IUD side (5) of the floating cone (40). The tube way (77) has an inner cylindrical path through which the graduated tube (16) passes clearly, while the floating cone (40) gets seated firmly in the tube way (77) like any known plug and a socket arrangement.

In the instrument (10) as per second embodiment that is ready to use, the string (31) is wrapped around the hook (43) by several turns, slid through the tubular hole (41) and the tubeway (77) taut, while the floating cone (40) is firmly plugged in the tubeway (77).

For use of the instrument (10) as per second embodiment, when the knob is made to slide towards the IUD end (5), the graduated tube (16) travels towards the IUD end (5), while the floating cone (40) continues to remain plugged in the tubeway (77). The dynamic stopper (20) also travels by the sliding length (23) while the graduated tube (16) engulfs the arms (34) of the IUD (30) till the edge (11) of the graduated tube (16) is stopped by the dome shaped ends (36) of the arms (34) having come almost together. Further sliding of the knob (150) towards the IUD end (5) causes the carriage (140) to also move towards the IUD end (5), and consequently the pushrod (17) also correspondingly moves. The string (31) is unwrapped from over the hook (43) and the floating plug (40) gets plugged out, and the string (31) is in the unlocked or the released condition.

FIGS. 21, 21A, 21B, 21C, in yet another embodiment, the string management (110) comprises an extended receptacle (145) with an open side (145A) on the operator side (6) of the carriage (140), and an end plug (78) with a slit (79) integratedly provided on the operator end (6) of the base (70).

In the instrument (10) as per third embodiment that is ready to use, the string (31) emerges out of the extended receptacle (145), taut, sits on the slit (79), and emerges out of an opening (89) of the base (70) while the extended receptacle (145) is firmly mounted on the end plug (78), keeping the string (31) in the locked condition.

For use of the instrument (10) as per third embodiment, when the operating knob (150) is made to slide towards the IUD end (5), the graduated tube (16) travels towards the IUD end (5), while the carriage (140) and therefore the extended receptacle (145) continues to remain mounted on the end plug (78). The dynamic stopper (20) also travels by the sliding length (23) while the graduated tube (16) engulfs the arms (34) of the IUD (30) till the edge (11) of the graduated tube (16) is stopped by the dome shaped ends (36) of the arms (34) having come almost together. Further sliding of the operating knob (150) towards the IUD end (5) causes the carriage (140) to also move towards the IUD end (5), and consequently the pushrod (17) also correspondingly moves. The extended receptacle (145) now gets dismounted from the end plug (78), string (31) is untrapped from an in-between of the end plug (78) and the extended receptacle (145), and thus the string (31) is in the unlocked or the released condition.

FIG. 20, 20A, 20B, 20C, there is provided at least one outpoint (87) and one inpoint (88) on the floor (81) of the base (70). The outpoint (87) and the inpoint (88) is essentially a tapered hole. The string (31) exits from the outpoint (87) and re-enters from the inpoint (88). The string (31) is accessible to the medical service provider between the outpoint (87) and the inpoint (88) and the medical service provider has a preferred option to trim the string (31) as per sounding measurement of uterus of woman, BEFORE inserting the graduated tube (16) in the cervix thereby avoiding use of scissors or cutting tool inside vaginal cavity, and this is most desired, safer and therefore preferred way of using the instrument (10) as per the present invention. The outpoint (87) is at a trim length (46) which is a minimum recommended excess string length expected to be hanging outside cervical os (51) in vaginal cavity of woman. The inpoint (88) is at a conservative length (47). Medical service provider has the freedom to trim the string (31) anywhere within the conservative length (47). A scale (48) is provided alongside to facilitate precision in trimming.

It is to be noted that the invention of string trimming before insertion is of significant benefit for instruments suited for all and any kind of IUD (30, 30A, 30B) and not limited to T-shaped IUD's, and this is an important ingredient of our invention. This ingredient of invention also implies that during release of the IUD (30, 30A, 30B), the instrument (10) handles much lesser length of string (31) than the prior art instruments wherein a long string (31) is always present till after release of IUD in uterus (50). It is known that a long string (31) has several occasions to undesirably interact with moving parts in the instrument (10) and may get entangled while withdrawing the IUD (30, 30A, 30B), and this possibility is completely obviated in our invention.

When the medical service provider uses the option of trimming the string (31) before insertion, the method to load the instrument (10) and safely place the IUD (30) in uterus (50) with above variations comprises the steps of:

a) Sounding a uterus (50) of woman and determining a uterine depth (45)

b) Sliding the operating knob (150) towards an IUD end (5) till the arms of the IUD (30) are folded and fully contained in the graduated tube (16), c) Sliding the operating knob (150) further towards the IUD end (5) till the graduated tube (16) projects out by a length of the uterine depth (45), judging by hearing an audible clicking sound produced due to the pair of locking tooth (148) negotiating with the array of inclines and notches (82) or judging by the measurement markings (14) on the graduated tube (16) aligning with the flange (25) or by the position of the pointer (158) of the operating knob (150) at the knob markings (95) on the cover (90), d) Trimming an excess length of the strings (31) of the IUD (30) anywhere in the conservative length (47), e) Inserting the graduated tube (16) in the uterus (50) till the flange (25) touches cervical os (51) of the uterus (50)

f) Sliding back the operating knob (150) till the dynamic stopper (20) retracts by the sliding length (23) and stops, g) Further inserting the graduated tube (16) in the uterus (50) till the flange (25) of retracted dynamic stopper (20) again touches the cervical os (51)

h) Sliding back the operating knob (150) as much as possible, and i) Taking out the graduated tube (16) and the instrument (10) from woman.

Figure 21:
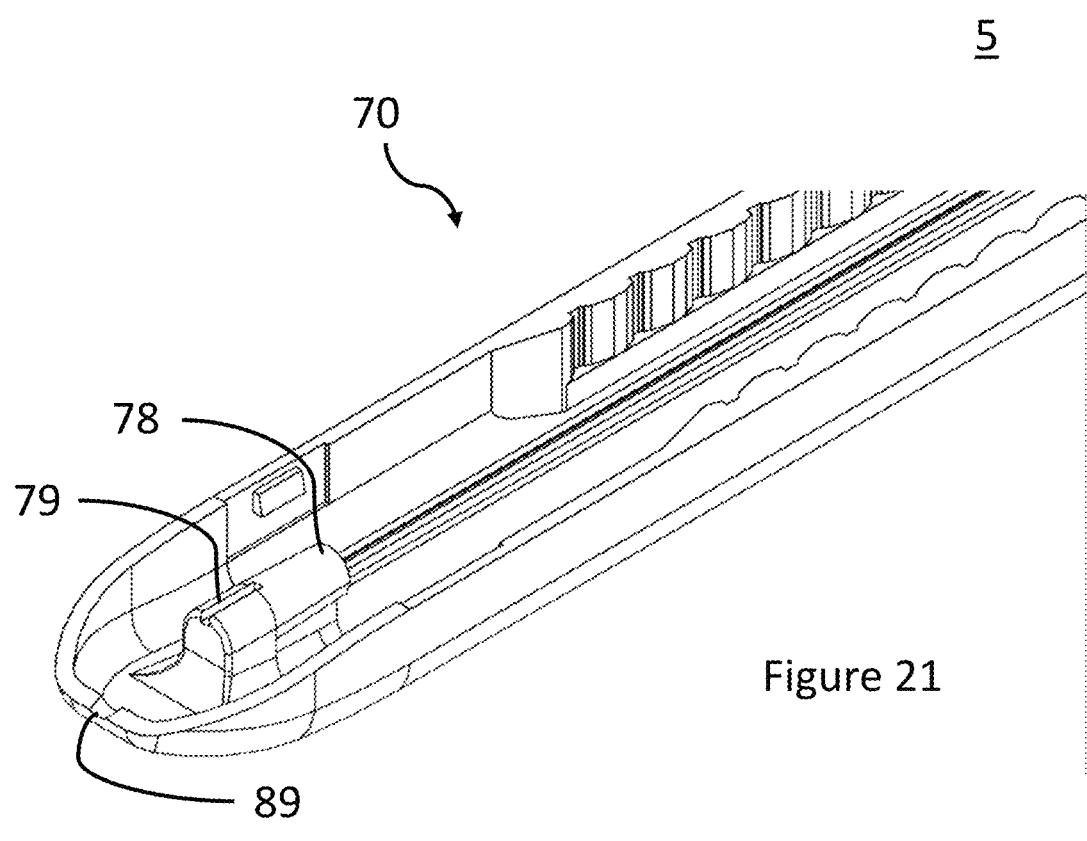
Figure 21A:
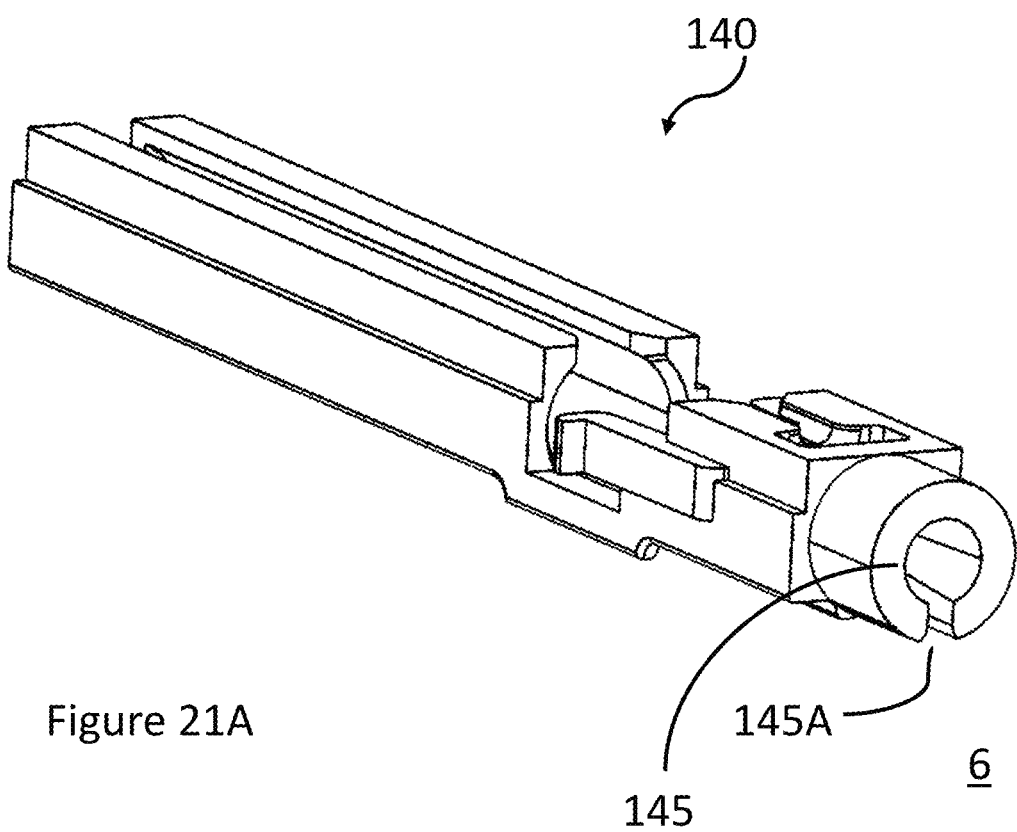
Figure 21B:
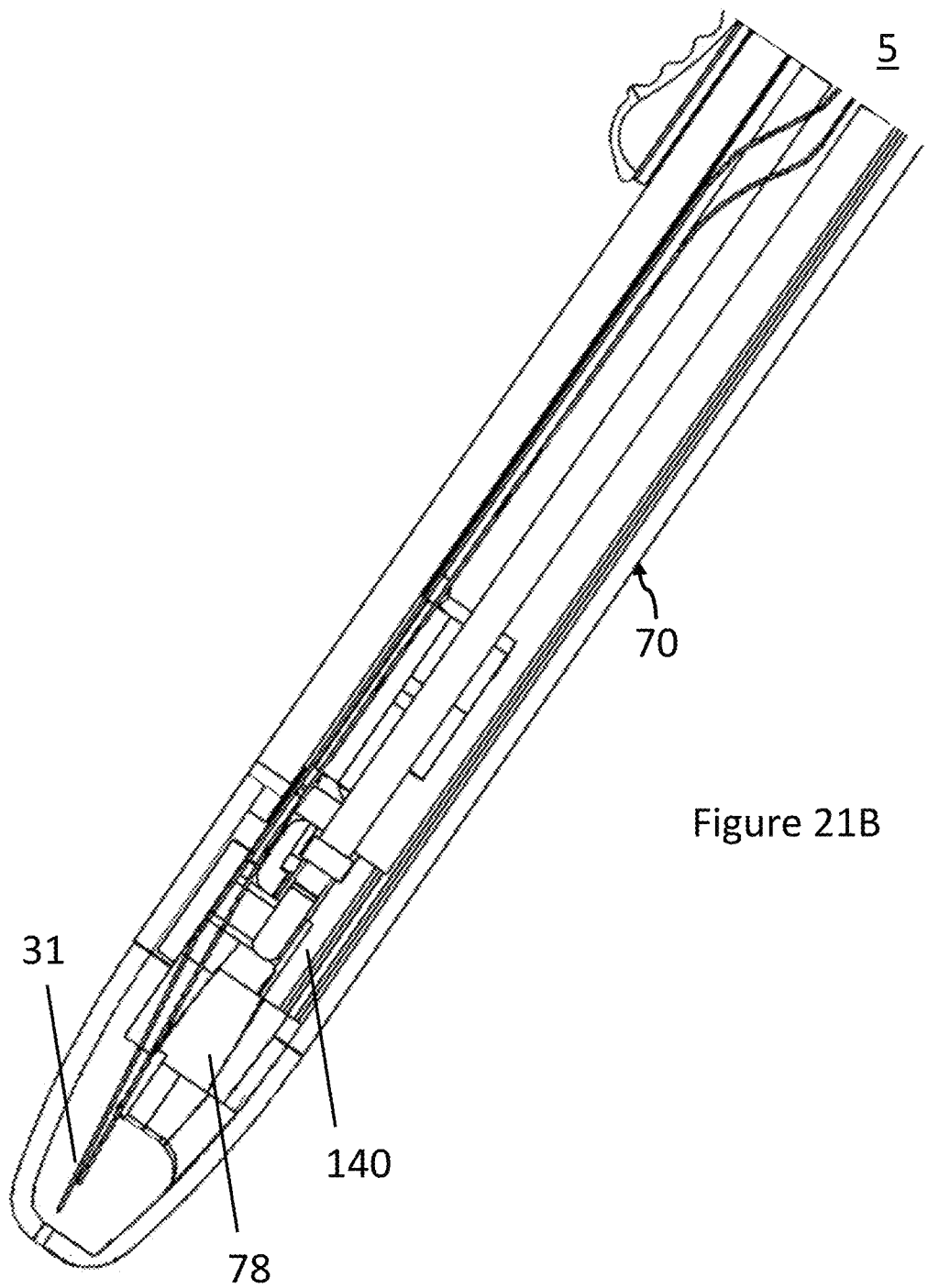
FIGS. 21B and 21C are partial sectional views of a third embodiment of the string management arrangement.
Figure 21C:
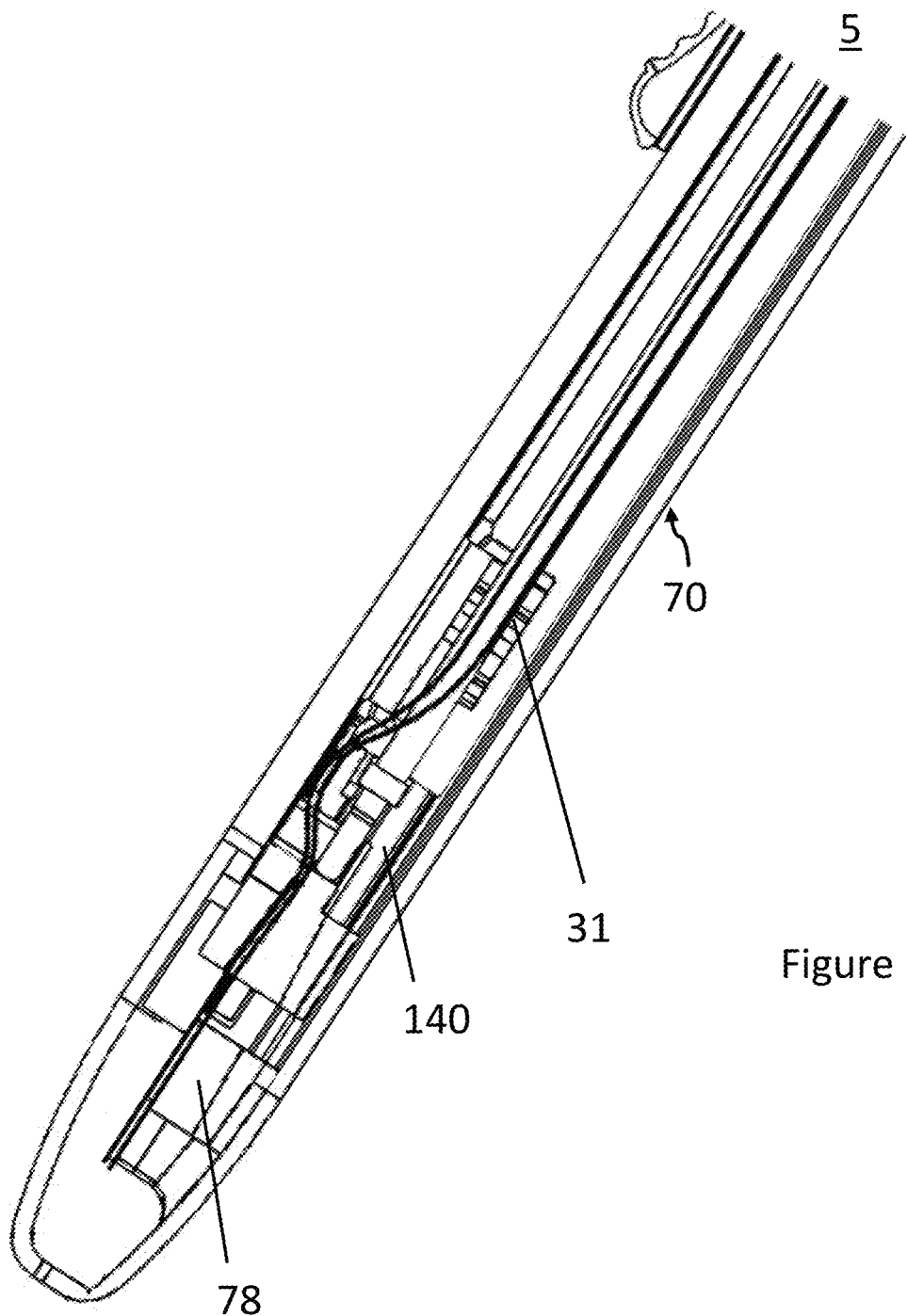

FIG. 21, as another variation, the base (70) has an out opening (89) through which the string (31) is still available to the medical service provider. The medical service provider can exercise the option to manually load the IUD (30) if that suits the service provider as per his or her previous experience or convenience.

Figure 22:
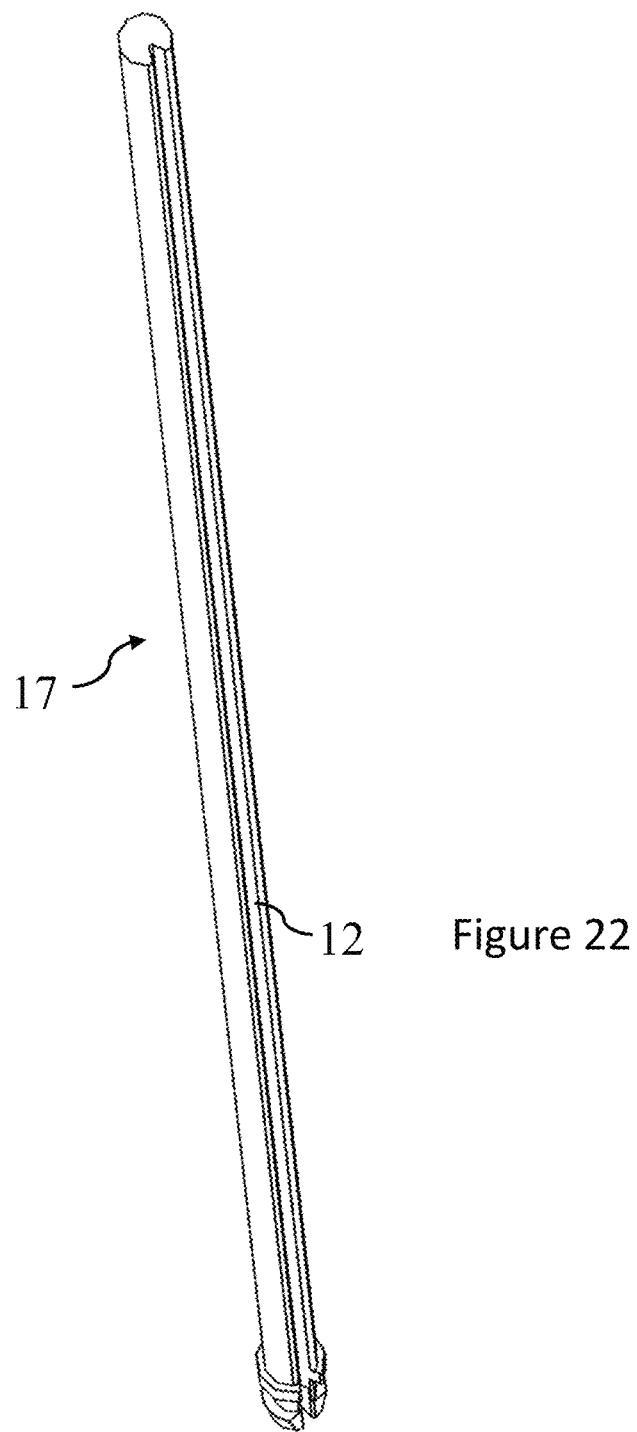
FIG. 22 is a perspective view of the push rod as per another embodiment.

FIG. 22, as yet another variation the push rod (17) has a longitudinal channel (12) or an equivalent construction to protect and shield the string (31) from getting entangled in the graduated tube (16).

The invention as described above can be worked with a permutation and combination of embodiments described above and the variations described are not mutually exclusive in any particular group or formation.

The instrument (10) operates from its either side, whether curvature up or curvature do while maintaining a horizontal orientation.

We claim:

1. An instrument (10) configured to prepare and safely place an intra-uterine device in uterus (50) of a woman, the instrument (10) comprising a "T" shaped intra-uterine device (IUD) (30) with both arms (34) foldable away from a stem (33) of the IUD (30),
   a graduated tube (16), a push rod (17) inside the graduated tube (16), wherein the instrument (10) further comprises:
   a dynamic stopper (20) with a tubular channel (22) and a flange (25), wherein a sliding length (23) of the dynamic stopper (20) is commensurate with an arm length (38) of the arms (34) of the IUD (30);
   a string management arrangement (110) whereby a string (31) of the IUD (30) is in one of a locked condition or an unlocked condition; and
   an operating device (100), further comprising
      a base (70) having an array of continuous inclines and notches (82) alternately for a prescribed length (83), a plurality of cover engagement means (74), a tube guideway (84), a first flange guiding projections (72), a carrier guiding projections (73),
      a cover (90) having a slot (91), a plurality of base engagement means (94) equal in number of the cover engagement means (74), a knob (150), a knob markings (95),
      a carriage (140) having a travel slot (143), at least a pair of locking tooth (148) on either carrier side, a pushrod passageway (147) with a seat (146),
      an operating knob (150) having at least a pointer (158), a hanging tubular construction (152) with a larger diameter part (153) along with a pusher (156) and a smaller diameter part (154);

wherein,
   the pushrod (17) has a collar (18) and a reversibly collapsible fitment means (19) at an operator end (6) and a flat surface (13) at an IUD end (5), and
   the graduated tube (16) having an edge (11) at the IUD end (5), a measurement markings (14) and a string exit slot (15);

wherein,
   the dynamic stopper (20) slidably resides in the base (70) and can slide by the sliding length (23), an operator end (6) of the graduated tube (16) is slid through the tubular channel (22) of the dynamic stopper (20), till the operator end (6) of the graduated tube (16) is disposed firmly in the larger diameter part (153) of the knob (150), the dynamic stopper (20) rides on the graduated tube (16), the hanging tubular construction (152) of knob (150) resides in the travel slot (143) of the carrier (140), the push rod (17) resides inside the graduated tube (16) with the reversibly collapsible fitment means (19) of the pushrod (17) pushed in the pushrod passageway (147) such that the collar (18) of the pushrod (17) sits in the seat (146) of the carrier (140); and when the knob (150) is made to slide towards the IUD end (5), the graduated tube (16) and the dynamic stopper (20) also travel towards the IUD end (5), the dynamic stopper (20) travels by the sliding length (23) while the graduated tube (16) engulfs the arms of the IUD till the edge (11) of the graduated tube (16) is stopped by the dome shaped ends (36) of the arms (34) while the string (31) remains in the locked condition, a further sliding of the knob (150) towards the IUD end (5) causes the carrier (140) to also move towards the IUD end (5), the pushrod (17) correspondingly moves while the string (31) is in the unlocked condition, a forward and a backward movement of the operating knob (150) by a sliding force on a thumb surface (159), the instrument (10) configured for a single hand grip as well as configured to move the knob (150) by a thumb of the same hand.

2. The instrument (10) configured to prepare and safely place the intra-uterine device (30) as claimed in claim 1, wherein the base (70) has at least one outpoint (87) and one inpoint (88), wherein the string (31) exits from the outpoint (87) and re-enters from the inpoint (88).

3. The instrument (10) configured to prepare and safely place the intra-uterine device (30) as claimed in claim 2, wherein the outpoint (87) is at a trim length (46) which is a minimum recommended excess string (31) length configured to be hanging outside a cervical os (51) in vaginal cavity of woman.

4. The instrument (10) configured to prepare and safely place the intra-uterine device (30) as claimed in claim 2, wherein the inpoint (88) is at a conservative length (47).

5. The instrument (10) configured to prepare and safely place the intra-uterine device (30) as claimed in claim 2, wherein the outpoint (87) and the inpoint (88) have a scale (48) alongside.

6. The instrument (10) configured to prepare and safely place the intra-uterine device (30) as claimed in claim 2, wherein the base (70) is curvatured, and the cover (90) is curvatured correspondingly.

7. The instrument (10) configured to prepare and safely place the intra-uterine device (30) as claimed in claim 1, wherein the string management arrangement (110) comprises a string plug (144) of the carriage (140) and a string socket (75) with a hole (76) on the base (70), the instrument (10) that is ready to use has the string (31) passed through the hole (76), taut, the string plug (144) plugged into the string socket (75), the string (31) therefore is in the locked condition; a movement of the carriage (140) towards the IUD end (5) causes the string plug (144) to move away and unplug from the string socket (75), the string (31) consequently is in the unlocked condition.

8. The instrument (10) configured to prepare and safely place the intra-uterine device (30) as claimed in claim 1, wherein the string management (110) comprises a floating cone (40) floatingly disposed on the graduated tube (16) and a tubeway (77) integratedly provided on the base (70), wherein the floating cone (40) has a tubular hole (41) on an inside, a conical frustum (42) on an outside and a hook (43) on an IUD end (5) of the floating cone (40), while the tube way (77) has an inner cylindrical path through which the graduated tube (16) passes clearly, while the floating cone (40) gets seated firmly, the instrument (10) that is ready to use has the string (31) wrapped around the hook (43), slid through the tubular hole (41) and the tubeway (77) taut, while the floating cone (40) is firmly plugged in the tubeway (77), the string (31) continues to stay in the locked condition, and when the knob (150) is made to slide towards the IUD end (5), the floating cone (40) continues to remain plugged in the tubeway (77), a further sliding of the knob (150) towards the IUD end (5) causes the carriage (140) to also move towards the IUD end (5), and consequently the pushrod (17) also correspondingly moves, the string (31) is unwrapped from over the hook (43) and the floating cone (40) gets plugged out, and the string (31) is in the unlocked condition.

9. The instrument (10) configured to prepare and safely place the intra-uterine device (30) as claimed in claim 1, wherein the string management (110) comprises an extended receptacle (145) with an open side (145A) on an operator side (6) of the carriage (140), and an end plug (78) with a slit (79) integratedly provided on the operator end (6) of the base (70), in the instrument (10) ready to use, the string (31) emerges out of the extended receptacle (145), taut, sits on the slit (79), and emerges out of an opening (89) of the base (70) while the extended receptacle (145) is firmly mounted on the end plug (78), keeping the string (31) in the locked condition; a movement of the carriage (140) towards the IUD end (5) causes the extended receptacle (145) to move away and dismount from the end plug (78), the string (31) is consequently in the unlocked condition.

10. The instrument (10) configured to prepare and safely place the intra-uterine device (30) as claimed in claim 1, wherein the dynamic stopper (20) further comprises a non-circular outer faces of lesser mating perimeter than that of the flange (25), there are provided guide paths (21) at least on two alternate faces of the dynamic stopper (20), wherein a face distance (26) of the tubular channel (22) permits a multi-point contact with the graduated tube (16) and allows a passage of the graduated tube (16) tightly.

11. The instrument (10) configured to prepare and safely place the intra-uterine device (30) as claimed in claim 1, wherein the carriage (140) further comprises a knob assembly opening (143A) which is wider than the travel slot (143) and a travel surface (149) on a lower side (142) of the carriage (140).

12. The instrument (10) configured to prepare and safely place the intra uterine device (30) as claimed in claim 1, wherein the base (70) has an out opening (89) through which a terminating end (35) of the string (31) emerge out.

13. The instrument (10) configured to prepare and safely place the intra-uterine device (30) as claimed in claim 1, wherein the push rod (17) has a longitudinal channel (12) along a length (17A) of the push rod (17).

14. A method to load an instrument (10) configured to prepare and safely place an intra-uterine device (30, 30A, 30B) in uterus (50) of a woman comprises the steps of:
   a) Sliding an operating knob (150) towards an IUD end (5) till arms (34) of the IUD (30) are folded and fully contained in a graduated tube (16),
   b) Sliding the operating knob (150) further towards the IUD end (5) till the graduated tube (16) projects out by a length of a uterine depth (45), judging by hearing an audible clicking sound produced due to the pair of locking tooth (148) negotiating with an array of inclines and notches (82) or judging by measurement markings (14) on the graduated tube (16) aligning with a flange (25) or by the position of a pointer (158) of the operating knob (150) at knob markings (95) on a cover (90),
   c) Inserting the graduated tube (16) in the uterus (50) till the flange (25) touches cervical os (51) of the uterus (50),
   d) Sliding back the operating knob (150) till a dynamic stopper (20) retracts by a sliding length (23) and stops,
   e) Further inserting the graduated tube (16) in the uterus (50) till the flange (25) of retracted dynamic stopper (20) again touches the cervical os (51),
   f) Sliding back the operating knob (150) as much as possible,
   g) Taking out the graduated tube (16) from woman, and
   h) Trimming an excess length of a string (31) of the IUD (30).

15. A method to load an instrument (10) configured to prepare and safely place an intra-uterine device (30, 30A, 30B) in uterus (50) of a woman comprises the steps of:
   a) Sliding an operating knob (150) towards an IUD end (5) till arms of the IUD (30) are folded and fully contained in a graduated tube (16),
   b) Sliding the operating knob (150) further towards the IUD end (5) till the graduated tube (16) projects out by a length of a uterine depth (45), judging by a clicking sound produced due to a pair of locking tooth (148) negotiating with an array of inclines and notches (82) or judging by measurement markings (14) on the graduated tube (16) aligning with a flange (25) or by a position of a pointer (158) of the operating knob (150) at the knob markings (95) on a cover (90),
   c) Trimming an excess length of strings (31) of the IUD (30) anywhere in a conservative length (47),
   d) Inserting the graduated tube (16) in the uterus (50) till the flange (25) touches cervical os (51) of the uterus (50),
   e) Sliding back the operating knob (150) till a dynamic stopper (20) retracts by a sliding length (23) and stops,
   f) Further inserting the graduated tube (16) in the uterus (50) till the flange (20) of retracted dynamic stopper (20) again touches the cervical os (51),
   g) Sliding back the operating knob (150) as much as possible, and
   h) Taking out the graduated tube (16) from woman.

* * * * *